US009903874B2

(12) United States Patent
Kurosawa et al.

(10) Patent No.: US 9,903,874 B2
(45) Date of Patent: Feb. 27, 2018

(54) METHOD OF DETERMINING RESISTANCE TO INFLUENZA VIRUS

(71) Applicant: Fujita Health University, Toyoake-shi (JP)

(72) Inventors: Yoshikazu Kurosawa, Toyoake (JP); Nobuko Ohshima, Toyoake (JP)

(73) Assignee: FUJITA HEALTH UNIVERSITY, Toyoake-Shi (JP)

( * ) Notice: Subject to any disclaimer, the term of this patent is extended or adjusted under 35 U.S.C. 154(b) by 0 days.

(21) Appl. No.: 14/913,879

(22) PCT Filed: Aug. 18, 2014

(86) PCT No.: PCT/JP2014/071591
§ 371 (c)(1),
(2) Date: Feb. 23, 2016

(87) PCT Pub. No.: WO2015/025825
PCT Pub. Date: Feb. 26, 2015

(65) Prior Publication Data
US 2016/0202265 A1    Jul. 14, 2016

(30) Foreign Application Priority Data

Aug. 23, 2013    (JP) .................................. 2013-172902

(51) Int. Cl.
*G01N 33/68*    (2006.01)
*G01N 33/569*    (2006.01)
*C07K 16/10*    (2006.01)

(52) U.S. Cl.
CPC ....... *G01N 33/686* (2013.01); *C07K 16/1018* (2013.01); *G01N 33/56983* (2013.01); *C07K 2317/21* (2013.01); *C07K 2317/55* (2013.01); *C07K 2317/565* (2013.01); *C07K 2317/76* (2013.01); *G01N 2333/11* (2013.01)

(58) Field of Classification Search
None
See application file for complete search history.

(56) References Cited

PUBLICATIONS

Oshima et al., J Virol. 2011, vol. 85, pp. 11048-11057.*
Wrammert et al., J Exp Med 201 vol. 208, pp. 9047-9052.*
Skehel, J.J. et al., "Receptor binding and membrane fusion in virus entry: the influenza hemagglutinin," Ann. Rev. Biochem. 69, 2000, pp. 531-569.
Knossow, M. et al. "Mechanism of neutralization of influenza virus infectivity by antibodies," Virology 302, 2002, pp. 294-298.
Okuno, Y. et al., "A common neutralizing epitope conserved between the hemagglutinins of influenza A virus H1 and H2 strains," J. Virol. 67, 1993, pp. 2552-2558.
Fraser, C. et al. "Pandemic potential of a strain of influenza A (H1N1): early findings," Science 324, 2009, pp. 1557-1561 and Supporting Online Material.
Hancock, K. et al., "Cross-reactive antibody responses to the 2009 pandemic H1N1 influenza virus," N. Engl. J. Med. 361, 2009, pp. 1945-1952 and Supplementary Appendix.
Wrammert, J. et al. "Broadly cross-reactive antibodies dominate the human B cell response against 2009 pandemic H1N1 influenza virus infection," J. Exp. Med. 208, 2011, pp. 181-193 and Supplemental Information.
Li, G.M. et al. "Pandemic H1N1 influenza vaccine induces a recall response in humans that favors broadly cross-reactive memory B cells," Proc. Natl. Acad. Sci. 109, 2012, pp. 9047-9052 and supporting information.
Ohshima, N. et al., "Naturally Occurring Antibodies in Humans Can Neutralize a Variety of Influenza Virus Strains, Including H3, H1, H2, and H5," J. Virol. , vol. 85, No. 21, 2011, pp. 11048-11057.
Lingwood, D. et al, "Structural and genetic basis for development of broadly neutralizing influenza antibodies," Nature, vol. 489, No. 7417, Sep. 27, 2012, pp. 566-570.
International Search Report dated Dec. 16, 2014, issued for PCT/JP2014/071591.
The extended European search report dated Feb. 28, 2017 issued for corresponding European Patent Application No. 14838699.8.
W. Pos et al. "VH1-69 germline encoded antibodies directed towards ADAMTS13 in patients with acquired thrombotic thrombocytopenic purpura", Journal of Thrombosis and Haemostasis, vol. 7, No. 3, Mar. 1, 2009 (Mar. 1, 2009), pp. 421-428.
Visentini Marcella et al. "Hepatitis B virus causes mixed cryoglobulinaemia by driving clonal expansion of innate B-cells producing a VH1-69-encoded antibody", Clinical and Experimental Rheumatology, Pacini, Pisa, IT, vol. 34, No. 3, Suppl. 97, Jan. 20, 2016 (Jan. 20, 2016), pp. S28-S32.

* cited by examiner

*Primary Examiner* — Shanon A. Foley
*Assistant Examiner* — Myron G Hill
(74) *Attorney, Agent, or Firm* — Locke Lord LLP; James E. Armstrong, IV; Nicholas R. Herrel

(57) ABSTRACT

Provided is a method of providing an effective means as a countermeasure for handling a pandemic of an influenza virus. The resistance to a type A influenza virus is determined using, as an indicator, the presence or otherwise of antibodies using the VH1-69 gene in a biological sample originating from a subject.

6 Claims, 8 Drawing Sheets

Fig. 1

Fab-pp

|  | F082-001 | F082-332 | F082-341 | F082-020 | F082-351 | F082-122 | F082-104 | F082-208 | F082-109 | F082-352 | F082-003 | F082-105 | F082-290 | F082-380 | F082-317 | F082-254 | F082-022 |
|---|---|---|---|---|---|---|---|---|---|---|---|---|---|---|---|---|---|
| F082-001 | 107.0 | 87.7 | 96.0 | 100.1 | 99.6 | 96.5 | 96.7 | 96.1 | 97.2 | 96.0 | 98.7 | 99.0 | 81.3 | 96.5 | 80.0 | 96.7 | 52.5 |
| F082-332 | 89.1 | 89.8 | 92.9 | 94.2 | 84.6 | 93.4 | 88.4 | 81.8 | 92.6 | 93.5 | 93.2 | 93.5 | 95.5 | 91.9 | 96.7 | 92.6 | 69.4 |
| F082-341 | 90.7 | 90.1 | 99.0 | 97.7 | 95.6 | 94.7 | 94.3 | 102.1 | 96.2 | 97.6 | 99.7 | 100.3 | 92.6 | 96.1 | 99.9 | 95.6 | 72.7 |
| F082-020 | 100.1 | 100.0 | 100.2 | 100.3 | 102.5 | 98.2 | 97.1 | 108.9 | 99.8 | 97.7 | 99.4 | 99.7 | 92.8 | 96.5 | 100.1 | 60.8 | 84.3 |
| F082-351 | 91.5 | 103.1 | 101.2 | 104.8 | 99.9 | 96.1 | 100.7 | 107.8 | 101.6 | 99.2 | 102.5 | 102.2 | 95.9 | 100.4 | 100.7 | 94.9 | 88.1 |
| F082-122 | 72.4 | 84.9 | 87.5 | 86.5 | 71.4 | 93.5 | 71.2 | 71.1 | 86.1 | 89.7 | 87.7 | 84.2 | 87.9 | 82.7 | 94.1 | 94.3 | 63.5 |
| F082-104 | 100.7 | 92.2 | 97.8 | 97.6 | 99.2 | 89.9 | 96.7 | 98.7 | 72.6 | 97.7 | 97.9 | 97.2 | 95.2 | 96.6 | 98.6 | 85.6 | 72.5 |
| F082-208 | 87.7 | 94.3 | 94.7 | 96.1 | 91.9 | 95.6 | 95.8 | 96.0 | 96.9 | 96.6 | 96.9 | 97.1 | 93.6 | 94.9 | 97.1 | 91.3 | 39.9 |
| F082-109 | 92.4 | 98.4 | 94.3 | 97.1 | 93.2 | 94.3 | 94.2 | 103.3 | 96.5 | 96.6 | 97.0 | 97.3 | 86.9 | 96.1 | 99.3 | 92.7 | 74.4 |
| F082-352 | 93.0 | 101.8 | 98.4 | 99.5 | 88.6 | 92.3 | 96.0 | 92.7 | 97.2 | 96.5 | 98.3 | 98.9 | 94.1 | 94.5 | 97.3 | 91.7 | 87.5 |
| F082-003 | 98.2 | 81.1 | 96.5 | 89.6 | 90.3 | 90.6 | 79.9 | 89.6 | 88.4 | 92.4 | 85.6 | 86.6 | 71.8 | 89.3 | 97.4 | 95.0 |  |
| F082-105 | 93.6 | 99.0 | 99.1 | 96.0 | 101.1 | 95.8 | 95.3 | 102.6 | 98.1 | 97.9 | 98.0 | 97.7 | 89.7 | 97.2 | 99.3 | 97.8 | 60.3 |
| F082-290 | 90.1 | 96.0 | 76.3 | 79.2 | 97.9 | 97.2 | 100.2 | 98.7 | 100.6 | 78.1 | 99.3 | 101.7 | 95.4 | 97.4 | 87.2 | 86.0 | 88.8 |
| F082-380 | 91.8 | 85.4 | 95.1 | 92.0 | 79.6 | 78.1 | 86.6 | 79.8 | 91.9 | 88.0 | 89.7 | 90.6 | 79.4 | 85.3 | 94.1 | 79.8 | 87.2 |
| F082-317 | 76.6 | 87.2 | 74.9 | 82.1 | 71.3 |  | 89.6 | 84.0 | 80.9 | 82.2 | 77.7 | 84.0 | 82.8 | 83.9 | 90.4 | 87.6 |  |
| F082-254 | 79.6 | 81.0 | 72.7 | 50.1 | 83.8 | 87.8 |  |  |  | 57.3 | 82.8 | 67.2 | 57.4 | 63.7 | 84.6 |  |  |
| F082-022 | 79.2 | 86.7 | 72.0 | 52.6 | 64.7 | 81.7 | 52.5 | 57.9 | 79.8 | 82.0 | 71.6 | 79.7 | 77.2 | 73.7 | 91.2 | 89.2 |  |
| F008-009 |  |  |  |  |  |  |  |  |  |  |  |  |  |  |  |  |  |
| F033-367 |  |  |  |  |  |  |  |  |  |  |  |  |  |  |  |  |  |

(row labels: Fab-cp3)

| Date of blood collection | A/Suita/1/2009H1N1pdm | | A/Brisbene/59/2007(H1N1) | | | A/Indonesia/5/2005(H5N1) | | |
|---|---|---|---|---|---|---|---|---|
| | HI | VN 50 | HI | VN 50 | M-VN 50 | HI | VN 50 | M-VN 50 |
| 2009.10.30 | <40 | <40 | <40 | 40 | 160 | <40 | <40 | ND |
| 2009.11.02 | <20 | 40 | <20 | 20 | 160 | <20 | <40 | ND |
| 2009.11.09 | <20 | 320 | <20 | 80 | 160 | <20 | <40 | ND |
| 2009.11.17 | 80 | 1280 | <20 | 80 | 320 | <20 | <40 | 40 |
| 2009.11.23 | 40 | 1280 | <20 | 80 | 320 | <20 | <40 | 40 |
| 2009.11.30 | 40 | 1280 | <20 | 80 | 320 | <20 | <40 | 40 |
| 2009.12.07 | 40 | 1280 | <20 | 80 | 320 | <20 | <40 | 40 |
| 2009.12.14 | 40 | 2560 | <40 | 80 | 320 | <40 | <40 | ND |

*Fig. 6*

|  | A/Suita/1/2009H1N1pdm | | | A/Brisbene/59/2007(H1N1) | | |
|---|---|---|---|---|---|---|
|  | Concentration of K1-18 (µg/mL) | | | Concentration of K1-18 (µg/mL) | | |
| Date of blood collection | 800 | 400 | 0 | 800 | 400 | 0 |
| 2009.11.02 | <40 | <40 | 40 | <20 | <20 | 20 |
| 2009.11.09 | 80 | 320 | 320 | <40 | <40 | 40 |
| 2009.11.17 | 640 | 640 | 1280 | 40 | 40 | 40 |
| 2009.11.03 | 320 | 640 | 2560 | 40 | 40 | 40 |
| 2009.12.07 | 320 | 640 | 2560 | 40 | 40 | 80 |
| 2009.12.14 | 320 | 320 | 2560 | <40 | 40 | 80 |

METHOD OF DETERMINING RESISTANCE TO INFLUENZA VIRUS

TECHNICAL FIELD

The present invention relates to an examination targeting an antibody. Specifically, the present invention relates to a method of determining resistance to an influenza virus using a specific antibody as an indicator. The present invention is useful as a countermeasure for handling an outbreak (pandemic) of influenza. The present application claims priority based on Japanese Patent Application No. 2013-172902 filed on Aug. 23, 2013, and the entirety of the contents of said patent application is herein incorporated by reference.

BACKGROUND ART

Influenza is an infectious disease of respiratory track that affects millions of people every year. Since antibodies (Abs) play important roles in protection against influenza virus, preventive vaccination has been the most efficient measure of influenza control. While hemagglutinin (HA) is the main target for virus-neutralizing Abs, it mediates virus entry into cells at two steps (Non-patent literature 1). First, HA binds to the cell receptor, sialic acid. After internalization of viruses by endocytosis, HA undergoes a drastic conformational change induced by low pH. It has been shown that neutralizing Abs have one of the following activities: prevention of binding reaction between HA and sialic acid (Non-patent literature 2) and prevention of low-pH-induced conformational change of HA (Non-patent literature 3). The former (hereinafter referred to as "1st type neutralizing Abs") binds to the site near sialic acid-binding pocket on the globular head in HA, and the latter binds to the stem region of HA. Since the dominant immune response is the first type, and mutations can be easily introduced into the target sites without losing the receptor-binding activity, variant viruses that have acquired resistance to these Abs become dominant and cause annual epidemics. Historically, it was long believed that all effective neutralizing Abs are the first type, and therefore, vaccine strains should have been changed almost every year in order to remain effective. As long as the type of vaccine strain well matches up to that of circulating virus, vaccination is effective for preventing virus infection.

Mode of response against infection of influenza virus is very heterogeneous among human population. For example, there are many persons who had suffered from influenza several times in their childhood but never suffered afterwards without vaccination. In 2009, a swine-origin H1N1 influenza virus (S-OIV) emerged and rapidly spread among human population, resulting in its classification as the first pandemic in the 21st century (Non-patent literature 4). It has been generally believed that humans lack immunity to the newly appearing influenza virus at the outbreak of pandemic because they are naive to the virus. In the case of S-OIV, however, long-lived memory B cells that produce broadly neutralizing Abs not only against seasonal H1N1 viruses but also S-OIV are found in many of the elderly (Non-patent literature 5 to 7).

PRIOR ART DOCUMENTS

Non-Patent Documents

Non-Patent Document 1: Skehel, J. J. & Wiley, D. C. Receptor binding and membrane fusion in virus entry: the influenza hemagglutinin. Ann. Rev. Biochem. 69, 531-569 (2000).

Non-Patent Document 2: Knossow, M. et al. Mechanism of neutralization of onfluenza virus infectivity by antibodies. Virology 302, 294-298 (2002).

Non-Patent Document 3: Okuno, Y., Isegawa, Y., Sasao, F. & Ueda, S. A common neutralizing epitope conserved between the hemagglutinins of influenza A virus H1 and H2 strains. J. Virol. 67, 2552-2558 (1993).

Non-Patent Document 4: Fraser, C. et al. Pandemic potential of a strain of influenza A (H1N1): early findings. Science 324, 1557-1561 (2009).

Non-Patent Document 5: Hancock, K. et al. Cross-reactive antibody responses to the 2009 pandemic H1N1 influenza virus. N. Engl. J. Med. 361, 1945-1952 (2009).

Non-Patent Document 6: Wrammert, J. et al. Broadly cross-reactive antibodies dominate the human B cell response against 2009 pandemic H1N1 influenza virus infection. J. Exp. Med. 208, 181-193 (2011).

Non-Patent Document 7: Li, G. M. et al. Pandemic H1N1 influenza vaccine induces a recall response in humans that favors broadly cross-reactive memory B cells. Proc. Natl. Acad. Sci. 109, 9047-9052 (2012).

SUMMARY OF THE INVENTION

Problems to be Solved by the Invention

Currently, the following countermeasures for a pandemic are taken in Japan.

(1) Stockpiling of a large amount of antiviral drug for influenza (a neuraminidase inhibitor)

(2) Stockpiling of a large amount of prepandemic vaccine (3) Construction of a system for the production of a pandemic vaccine Regarding (1), there are a problem that the term in which the antiviral drug for influenza is effective in the processes of infection and onset of disease is limited, and a problem of the emergence of a drug resistance virus. Regarding (2), there is a problem that the type (antigenicity) of a virus that actually causes a pandemic cannot be properly expected. Regarding (3), although switching from conventional proliferation of a virus in chicken egg to proliferation of a virus in cultured cells, there is a limit in shortening of a time for the production of a vaccine.

In order to make a breakthrough in the above-mentioned current situations, the present invention aims at providing an effective means as a countermeasure against a pandemic of an influenza virus.

Means for Solving Problem

In order to analyze total repertoire of neutralizing Abs against influenza viruses in humans, we developed the following experimental strategy in our previous study (Reference 8). A large number of B lymphocytes are collected by apheresis from a donor, and a huge Ab library is constructed by using the phage-display technology. The library is screened with formalin-treated virus particles. The clones that have both binding activity and neutralizing activity to the virus are isolated and their strain specificity is extensively characterized. Although only B lymphocytes that are circulating in peripheral blood are analyzed in our experimental system, the results obtained appeared to represent the total repertoire of neutralizing Abs formed in the donor's body (Reference 8). We applied this strategy to extensively analyzed total repertoire of antibodies against HA that were induced in the body of such a person after vaccination with 2009 H1N1 pandemic influenza virus. They are classified into two types with few exceptions. The first type, the products by B cells newly induced through vaccination, binds to the surroundings of a sialic acid-binding pocket. The second type, the products by long-lived memory B cells established before vaccination, utilized 1-69 $V_H$ gene, binds to the stem of HA. The second type neutralizes both H1N1 and H5N1 viruses. Furthermore, it was suggested that it is highly possible that the second type antibody has recognized an epitope that is difficult to change, and thus respond to the virus infection for a long term. Considering the above-mentioned results, a strategy to prepare for a pandemic of influenza should be designed with consideration for an antibody possessed by an individual person (an effective neutralization antibody, that is, the presence or absence of possession of the second type antibody), and it can be said that "an antibody using VH1-69 gene" is useful as an indicator therefor. That is, if an antibody using VH1-69 gene is detected and the result thereof is utilized, then an effective and efficient countermeasure for a pandemic can be attained. In addition, it was also clarified by the consideration of the present inventors that the antibody using VH1-69 gene can be detected as a secreted antibody, that the antibody using VH1-69 gene increases by vaccination, and the like, and it was directly shown that the antibody using VH1-69 gene functions as a neutralization antibody by the fact that a monoclonal antibody (K1-18), which inhibits the binding of the antibody using VH1-69 gene and hemagglutinin, inhibited the virus neutralizing activity.

Based mainly on the above-mentioned results, the following inventions are provided.

[1] A method of determining resistance to a type A influenza virus by using the presence or absence of an antibody using VH1-69 gene in a biological sample derived from a subject.

[2] The method according to [1], including the following steps (1) to (3):

(1) a step of bringing a biological sample of a subject that has received an influenza vaccine into contact with an anti-ideotype antibody that recognizes an antibody using VH1-69 gene;

(2) a step of detecting a generated immune complex;

(3) a step of determining the intensity of the resistance to the type A influenza virus based on the detection result in the step (2), in which the amount of the detected immune complex serves as an indicator of the intensity of the resistance to the type A influenza virus.

[3] The method according to [2], further including the following step:

(4) a step of detecting an immune complex generated by bringing a biological sample of a subject before receiving the influenza vaccine into contact with an anti-ideotype antibody that recognizes an antibody using VH1-69 gene, comparing the amount of the immune complex with the amount of the immune complex detected in the step (2), and determining the intensity of the resistance based on the result of the comparison.

[4] The method according to [2] or [3], in which the biological sample is a blood sample.

[5] The method according to any one of [1] to [4], in which the type A influenza virus is one or more viruses selected from the group consisting of H1N1, H1N2, H2N2, H3N2, H5N1, H5N2, H6N1, H7N2, H7N3, H7N7, H7N9, H9N2 and H9N1.

[6] The method according to any one of [1] to [4], in which the type A influenza virus is one or more viruses selected from the group consisting of H1N1, H2N2, H3N2 and H5N1.

[7] The method according to any one of [1] to [4], in which the type A influenza virus is one or more viruses selected from the group consisting of H1N1, H1N2, H2N2, H5N1 and H5N2.

[8] A kit for detecting resistance to a type A influenza virus, including an anti-ideotype antibody that specifically recognizes an antibody using VH1-69 gene.

BRIEF DESCRIPTION OF THE DRAWINGS

FIG. 1 Activities of representative clones classified into 63 groups. Numbers in the first three columns correspond to Group number of those isolated by the screenings, number of unique clones in each group, and number of isolated clones in each group, respectively. Germline gene was identified by comparison between the amino acid sequence of $V_H$ of the representative clone and those of all the germline $V_H$ genes, and the identity (%) was indicated. The amino acid sequence of CDR3 was shown. The binding activity to four H1N1 (NC99, SI06, Bri07 and Cal09) and one H3N2 virus particles was examined by ELISA. Absorbance at 492 nm was marked as follows: ≥1.00 (red), 0.50-0.99 (orange), 0.10-0.49 (yellow); The virus neutralizing activity of 100 or 250 μg/ml Fab-PP Ab against H1N1, H5N1, and H3N2 viruses was examined by the focus reduction test. The reduction rate was shown as percentage and marked as follows: ≥60% (dark blue), 40-60% (blue), 20-40% (light blue); The HI activity of Fab-PP Ab was measured using two H1N1 (Bri07 and Cal09) viruses. The lowest concentration (μg/ml) of Fab-PP Abs to inhibit hemagglutination was shown. The amino acid sequences of CDR3s are, from the top to the bottom, as follows: DTTVTNEEINFYYGMDV (SEQ ID NO:1), DTEVTNEEINFYYGMDV (SEQ ID NO:2), DTEVTSEEINFYYGMDV (SEQ ID NO:3), DTTVTSEEINFYQGMDV (SEQ ID NO:4), EFGANGEDIYFYHGMDV (SEQ ID NO:5), SIGGYDGEGIFYNHYGMDV (SEQ ID NO:6), DEWFGELGSSGMDV (SEQ ID NO:7), DFAGEGHGSGSVDY(SEQ ID NO:8), SATSYRDYLDRDFFYYALDV (SEQ ID NO:9), SATSYRDYLDRDFYYYALDV (SEQ ID NO:10), DHLNSEIVATITGFLDY(SEQ ID NO:11), DKLNSEMVATITGFLDY(SEQ ID NO:12), DKLNSEMVATITGFMDY(SEQ ID NO:13), DKLNSDEVTTITGFLDY(SEQ ID NO:14), DNLNSELVATITGFLDH(SEQ ID NO:15), DNLNSDEVATISGFLDY(SEQ ID NO:16), DYLNSEMVATITGFLDS(SEQ ID NO:17), EPSNTEDIRGIEGVFDY (SEQ ID NO:18), DAYSSGDTYYYGLDV (SEQ ID NO:19), DRGTGEQIAVVTALIDY(SEQ ID NO:20), HGYGDYVGYFDY(SEQ ID NO:21), VLRWLGEEDADAFDI (SEQ ID NO:22), GFGMVGDTVDDLYNGMDV (SEQ ID NO:23), VQRPYGDYAAGAFDI (SEQ ID NO:24), VQRPYGDYITGAFDI (SEQ ID NO:25), RTWYYDGSGPDPSRDAFDI (SEQ ID NO:26), DLGNGEDIAVQPGTIGVDY(SEQ ID NO:27), DLGNGEDIAVQPGTTGVDY(SEQ ID NO:28), DLGNGEDIVVQPATIGVDY(SEQ ID NO:29), GTEVTTEEIYFYYGMDV (SEQ ID NO:30), GTEVTTEEINFYYGMDV (SEQ ID NO:31), AEKWLADYFYYFGMDV (SEQ ID NO:32), DREESLFAGAIYNYYYDMDV (SEQ ID NO:33), KGGAKLLYFDWLASAFDI (SEQ ID NO:34), GPNYYENFFDY(SEQ ID NO:35), GPNYYESYFDY(SEQ ID NO:36), GPNYYENYFDF (SEQ ID NO:37), GPNYYESYLDF (SEQ ID NO:38), GPNYFESYFDN(SEQ ID NO:39), GPNYYETYLDN(SEQ ID NO:40), GPHYYESHLDY(SEQ ID NO:41), GPHYYVSYFDS(SEQ ID NO:42), GNTYYSSYFDQ (SEQ ID NO:43), GSTYYSSYFDQ (SEQ ID NO:44), SGTYYVSYFDS(SEQ ID NO:45), SGTYYVSYLDS(SEQ ID NO:46), SGTYYVSFFDY(SEQ ID NO:47), SGSYYPDYFQY(SEQ ID NO:48), SPTYYPGALDM (SEQ ID NO:49), APLIYN-WYFDL (SEQ ID NO:50), APLIYNWYYDL (SEQ ID NO:51), HPTYHYGSAMDY(SEQ ID NO:52), HPTYYF-GSAMEY(SEQ ID NO:53), HPTYYYGSPMDY(SEQ ID NO:54), HPMYHYGSAMDY(SEQ ID NO:55), HSGYH-LIGYFDS(SEQ ID NO:56), EEGYYYGSGPLDS(SEQ ID NO:57), NSGYHISGFYLDY(SEQ ID NO:58), SLGYHTQYNGMDV (SEQ ID NO:59), HPTYHFDKS-GYRFDS(SEQ ID NO:60), SRGYSFGYGTDYFDY(SEQ ID NO:61), NYYGSGTYFNDAFDI (SEQ ID NO:62), YQSSDYYNSEYFQH(SEQ ID NO:63)

FIG. 2 Competitive inhibition of binding to HA among the Abs newly induced by vaccination. The binding activity of Fab-PP Ab (indicated at upper side) to Cal09 virus particles was measured by ELISA under the presence of 10-times high concentration of Fab-cp3 Ab (indicated at the left side). F008-009 and F033-367 are not anti HA Abs and used as controls. The binding inhibition was calculated as follows: the absorbance value under the presence of F008-009cp3 was used as 100% binding and the degree of reduction in the absorbance value under the presence of Fab-cp3 of Ab was measured and shown as percent inhibition. Percent inhibition was marked as follows: ≥70% (white), 50-70% (grey), 0-50% (dark grey). The experiment was performed at least three times in duplicate.

Figure 5:
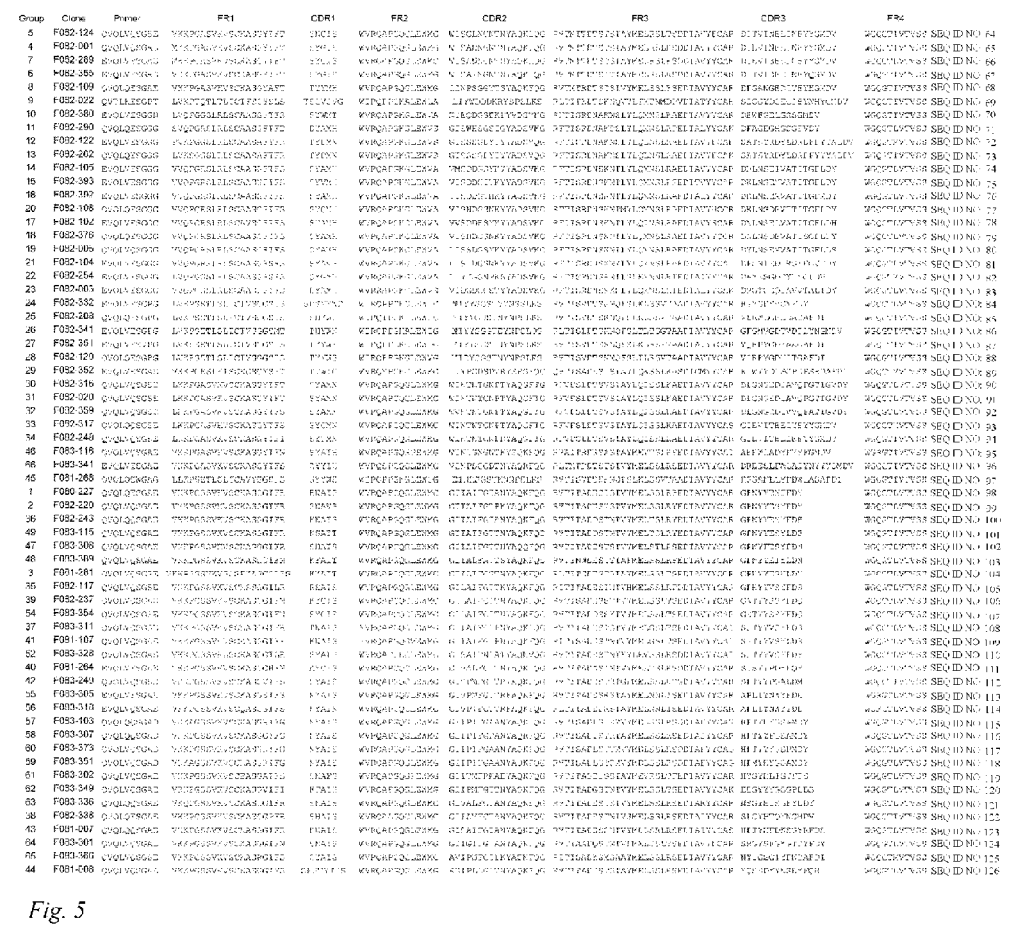

FIG. 5 The amino acid sequence of VH (FR1-CDR1-FR2-CDR3-FR4) of each clone. SEQ ID NOs are 64-126 from the top to the bottom.

FIG. 6 HI and virus neutralizing activity of serum against H1N1 and H5N1 viral strains. For measurement of virus neutralizing activity of serum, VN and M-VN method was used. The results were indicated as the reciprocal of the highest dilution of serum to inhibit hemagglutination for HI activity and to show 50% focus reduction rate for virus neutralization test. Serums before vaccination were 2009.10.30 and 2009.11.2. ND means not-determined.

FIG. 7 Virus neutralizing activity of serum in the presence of K1-18 Ab. The results were indicated as the reciprocal of the highest dilution of serum to show 50% focus reduction rate. Serum before vaccination was 2009.11.2.

DETAILED DESCRIPTION OF THE INVENTION

Figure 3:
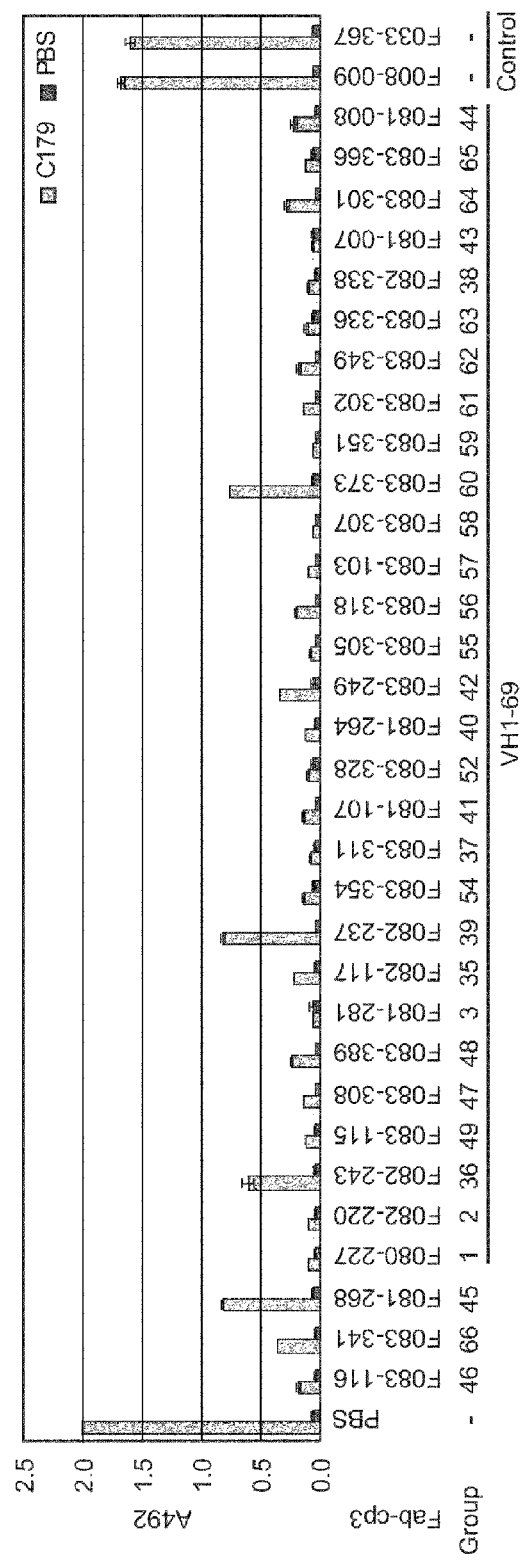
FIG. 3 Inhibition of the binding of C179 to HA by type 2 Abs isolated in this study. Binding of C179 to Bri07 virus particles was examined under presence of a 10-times high concentration of various Fab-cp3 Abs by ELISA. F008-009 and F033-367 are not anti HA Abs and used as negative controls. Group number was indicated under the name of clone. The experiment was performed two times in duplicate and the error bars show standard deviation.

1. Method for Determining Resistance Against Type A Influenza Virus

The first aspect of the present invention relates to a method for determining resistance to a type A influenza virus. According to the present invention, the resistance of a subject to a type A influenza virus can be determined by an objective indicator. The method of the present invention is effective as a means for a countermeasure for handling a pandemic of influenza which may occur in the future, and thus is of extremely great value. In the method of the present invention, the resistance of a subject to a type A influenza virus is determined by using the presence or absence of an antibody using VH1-69 gene in a biological sample derived from the subject as an indicator, based on the finding that an antibody using VH1-69 gene broadly shows a neutralizing activity against type A influenza viruses, and the finding that B cells that produce an antibody using VH1-69 gene remain as memory cells and play an important role in the protection of a living body from type A influenza (regarding the details, see the Examples mentioned below).

Type A influenza viruses are roughly classified into two groups depending on the types of HA molecules: group 1 consisting of H2, H5, H1 and H6 (these are H1 clusters; H1a) and H13, H16 and H11 (these are H1 clusters; H1b), and group 2 consisting of H8, H12 and H9 (these are H9 clusters), H4, H14 and H3 (these are H3 clusters) and H15, H7 and H10 (these are H7 clusters). The method of the present invention exhaustively targets these type A influenza viruses. However, in one embodiment, one or more viruses selected from the group consisting of H1N1, H1N2, H2N2, H3N2, H5N1, H5N2, H6N1, H7N2, H7N3, H7N7, H7N9, H9N2 and H9N1 is/are targeted. In another embodiment, one or more viruses selected from the group consisting of H1N1, H2N2, H3N2 and H5N1, which are specifically deemed to be in great need for a countermeasure for a pandemic, are targeted. Furthermore, in still another embodiment, group 1 viruses are targeted, based on the fact that an epitope that is shared among group 1 viruses was recognized by the respective antibodies using VH1-69 gene (the antibodies found in the sample derived from a subject in the experiment shown in the Examples). That is, in this embodiment, one or more viruses selected from the group consisting of H1N1, H1N2, H2N2, H5N1 and H5N2 is/are targeted.

In the determination method of the present invention, the presence or absence of an antibody using VH1-69 gene serves as an indicator. In other words, the resistance to a type A influenza virus is determined by the presence, amount, repertoire and the like of the antibody using VH1-69 gene.

A VH1-69 gene can generate an antibody that broadly shows a neutralizing activity by forming an antigen binding site even without a VL domain. "Antibody using VH1-69 gene" is an antibody having a VH region in which a VH1-69 gene, which is a Germline gene, is used. The VH1-69 gene codes for FR1, CDR1, FR2, CDR2 and FR3 that constitute the VH region. Accordingly, in "antibody using VH1-69 gene", high homology (commonality) is recognized in the amino acid sequence of from FR1 to FR3. Furthermore, the antibody using VH1-69 gene is characterized by the amino acid at the position 53 and the amino acid at the position 54, and this characteristic is considered to be important for the physiological function of "antibody using VH1-69 gene". In the antibody using VH1-69 gene, the amino acid residue at the position 53 is generally a hydrophobic amino acid (isoleucine, methionine, leucine, valine or the like), and the amino acid residue at the position 54 is also a hydrophobic amino acid (phenylalanine, leucine or the like). Typically, the position 53 amino acid of the antibody using VH1-69 gene is isoleucine, and the position 54 amino acid is phenylalanine. The sequence of the VH1-69 gene (coding for FR1 to FR3) is shown in SEQ ID NO: 127. Furthermore, the amino acid sequence encoded by the VH1-69 gene (FR1 to FR3) is shown in SEQ ID NO: 128.

The subject is not specifically limited, and humans of all ages may be the subject. The biological sample is also not specifically limited, and a biological sample in which an antibody can be detected is used. Examples of the biological sample are blood, blood plasma, blood serum, nasal secretion and saliva. Preferably, for the reasons of easy preparation, low invasiveness and the like, blood samples are used. Among the blood samples, it is specifically preferable to adopt blood serum or blood plasma as the sample. The biological sample may be prepared according to a conventional method.

In the method of the present invention, the following steps (1) to (3) are typically conducted.

(1) a step of bringing a biological sample of a subject that has received an influenza vaccine into contact with an anti-ideotype antibody that recognizes an antibody using VH1-69 gene;

(2) a step of detecting a generated immune complex;

(3) a step of determining the intensity of the resistance to a type A influenza virus based on the detection result in the step (2), in which the amount of the detected immune complex serves as an indicator of the intensity of the resistance to the type A influenza virus.

In the step (1), a biological sample of a subject that has received an influenza vaccine, which has been prepared in advance, is brought into contact with an anti-ideotype antibody that recognizes an antibody using VH1-69 gene. The step (1) is an antigen-antibody reaction in vitro, and if an antibody using VH1-69 gene is present in the biological sample, then an immune complex is formed with an anti-ideotype antibody.

Various viral strains can be used for the influenza vaccine. For example, inactivated vaccine, or live vaccines of H1N1 influenza (for example, A/California/7/2009pdm strain, A/Suita/1/2009pdm strain, A/New Caledonia/20/1999 strain, A/Solomon Islands/3/2006 strain, A/Brisbane/59/2007 (Bri07) strain), H3N2 influenza (for example, A/Panama/2007/1999 strain), H5N1 influenza (for example, A/Indonesia/5/2005/PR8-IBCDC-RG2 strain) can be used.

It is preferable to use a biological sample that has been collected at the timepoint when 5 days to 3 weeks have elapsed from vaccination so that the antibody that has been induced by the vaccination is sufficiently contained in the biological sample. A biological sample after plural times (for example, twice) of vaccination may also be used, and in such case, a biological sample that has been collected at the timepoint when 5 days to 3 weeks have elapsed from the final vaccination is generally used.

For the step (1), as a detection antibody, an anti-ideotype antibody that recognizes an antibody using VH1-69 gene is used. The anti-ideotype antibody is an antibody that specifically recognizes a complementarity-determining region (CDR) in an antibody, and an anti-ideotype antibody that is specific to an antibody using VH1-69 gene is used in the present invention. As mentioned above, the antibody using VH1-69 gene is characterized by the amino acid at the position 53 (typically isoleucine) and the amino acid at the position 54 (typically phenylalanine). Accordingly, it is preferable to use an anti-ideotype antibody that specifically recognizes regions including these amino acids. The anti-ideotype antibody used in the present invention may be prepared by using a known method, such as an immunological technique, a phage display process, a liposome display process or the like. There are companies or authorities for providing a service of contract preparation of antibodies (for example, Immuno-Biological Laboratories Co, Ltd. and APRO Science Inc.), and the anti-ideotype antibody may also be prepared by utilizing the service. The anti-ideotype antibody may be any of a polyclonal antibody, an oligoclonal antibody (a mixture of several to several tens of antibodies) and a monoclonal antibody, and a monoclonal anti-ideotype antibody is preferably used.

The biological sample and anti-ideotype antibody are brought into contact by adding the anti-ideotype antibody to the biological sample, or by adding the biological sample to an element (for example, a well) on which the anti-ideotype antibody has been immobilized, or the like. The specific embodiment of the contacting, the conditions for the contacting, and the like may be suitably preset depending on the measurement method to be adopted.

In the step (2), the immune complex generated by the step (1) is detected. As the detection method (measurement method), a latex agglutination method, a fluoroimmunoassay (FIA), an enzyme immunoassay (EIA), a radioimmunoassay (RIA) and a Western blotting can be exemplified. As preferable detection method, FIA and EIA (including ELISA) can be exemplified. According to these methods, the detection can be conducted at high sensitivity, rapidly and conveniently. In FIA, a fluorescence-labeled antibody is used, and the immune complex is detected by using fluorescence as a signal. On the other hand, in EIA, an enzymatically-labeled antibody is used, and the immune complex is detected by using color development or luminescence based on an enzymatic reaction. The process is not limited to a non-competitive process, and a competitive process may also be used.

In the step (3), the intensity of the resistance to the type A influenza virus is determined based on the detection result in the step (2). In the present invention, the amount of the immune complex detected during the determination is deemed as an indicator of the resistance to the type A influenza virus. Typically, the intensity of the resistance to the type A influenza virus is determined based on the amount of the detected immune complex. The determination herein can be conducted automatically/mechanically without the judgement of a person having specialized knowledge such as a medical practitioner or a laboratory technician, as is apparent from the determination criteria therefor. Examples of the specific determination criteria are shown below.

<Examples of Determination Criteria>

(a) If an immune complex is detected, then resistance to an type A influenza virus is present.

(b) If an immune complex is detected, then resistance to an type A influenza virus is intense.

(c) Resistance to an type A influenza virus is more intense at a larger amount of an immune complex.

(Example of Qualitative Determination 1)

When a detected value is higher than a criterion value, it is determined that "resistance to a type A influenza virus is present", whereas when a detected value is lower than a criterion value, it is determined that "resistance to a type A influenza virus is absent".

(Example of Qualitative Determination 2)

When a detected value is higher than a criterion value, it is determined that "resistance to a type A influenza virus is intense", whereas when a detected value is lower than a criterion value, it is determined that "resistance to a type A influenza virus is weak".

(Example of Qualitative Determination 3)

When detecable (in the case of positive), it is determined that "resistance to a type A influenza virus is present", whereas when undetecable (in the case of negative), it is determined that "resistance to a type A influenza virus is absent".

(Example of Qualitative Determination 4)

When detecable (in the case of positive), it is determined that "resistance to a type A influenza virus is intense", whereas when undetecable (in the case of negative), it is determined that "resistance to a type A influenza virus is weak".

(Example of Quantification Determination)

As shown below, the intensity of resistance is preset for every scope of detected values, and the resistance is determined from a detected value.

Measured value<a: resistance is absent a≤measured value<b: resistance is weak b≤measured value<c: resistance is present but is not sufficient c<measured value: resistance is intense Although the intensity is classified into four stages, the number of the classification can be optionally preset. An example of the number of the classification is from 2 to 7, preferably from 3 to 6.

In an embodiment of the present invention, the resistance to a type A influenza virus is determined by comparing the biological sample before vaccination and the biological sample after the vaccination. That is, this embodiment also includes the following step (4).

(4) A step of detecting an immune complex generated by bringing a biological sample of a subject before receiving the influenza vaccine into contact with an anti-ideotype antibody that recognizes an antibody using VH1-69 gene, comparing the amount of the immune complex with the amount of the immune complex detected in the step (2), and determining the intensity of the resistance based on the result of the comparison.

If increase in the amount of the immune complex is observed after the vaccination as a result of the comparison, it can be determined that the resistance to a type A influenza virus is intense. Furthermore, the responsiveness regarding the antibody using VH1-69 gene can also be figured out. Accordingly, by conducting the step (4), beneficial information, although it is auxiliary, can be obtained. Furthermore, in the case when the determination is conducted by the step (4), the subjects can be typically classified into the following four groups.

(a) Persons who have a large amount of an antibody using VH1-69 gene (a neutralization antibody against a type A influenza virus)

(b) Persons who have a small amount of an antibody using VH1-69 gene (a neutralization antibody against a type A influenza virus)

(c) Persons who do not have an antibody using VH1-69 gene (a neutralization antibody against a type A influenza virus)

(d) Persons for whom an antibody using VH1-69 gene (a neutralization antibody against a type A influenza virus) is not induced even after vaccination If the subjects are classified into (a) to (d) as mentioned above, for example, the following countermeasures can be taken for the respective groups, and thus extremely effective and efficient countermeasure for handling a pandemic can be attained.

Group (a): Basically, a countermeasure is not necessary.

Group (b): Selective stimulation of the proliferation of cells that produce a targeted neutralization antibody by inoculation of a H5N1 influenza vaccine Group (c): Induction of the production of a targeted neutralization antibody by inoculation of several kinds of different group 1 influenza virus vaccines.

Group (d): A human antibody that neutralizes group 1 influenza viruses is prepared as an antibody for prevention/treatment, and is admistered as necessary.

2. Kit for Determining Resistance to Influenza Virus

The second aspect of the present invention relates to a kit that is used in the determination method of the present invention. The kit of the present invention includes an anti-ideotype antibody that specifically recognizes an antibody using VH1-69 gene as a major constitutional element so as to detect or capture an antibody using VH1-69 gene. The anti-ideotype antibody has been labeled as necessary so as to be suitable for the use thereof. Examples of label substances that can be used for the labeling of the antibody can include fluorescent pigments such as fluorescein, rhodamine, Texas Red and Oregon Green; enzymes such as horseradish peroxidase, microperoxidase, alkaliphosphatase and β-D-galactosidase; chemical or biological luminescent compounds such as luminol and acridine pigments; radioisotopes such as $^{32}P$, $^{131}I$ and $^{125}I$; and biotin. A labeled secondary antibody that recognizes the anti-ideotype antibody can also be included in the kit. In this case, a non-labeled anti-ideotype antibody is generally used. The anti-ideotype antibody may be immobilized. The insoluble substrate used for the immobilization is not specifically limited. For example, resins such as polystyrene resins, polycarbonate resins, silicon resins and nylon resins, and a water-insoluble substance such as glass can be used. The immobilization of antibody can be carried by physical adsorption or chemical adsorption.

Other agents (buffers, solvents, blocking agents, substrates for enzyme, coloring agents and the like) and/or apparatuses or instruments (a container, a reaction apparatus, a fluorescence reader and the like) for use in carrying out the determination method of the present invention may also be included in the kit. Furthermore, an influenza strain that is used as a control, for the preparation of a calibration curve, and the like may also be included in the kit. In addition, an instruction manual is generally attached to the kit of the present invention.

EXAMPLES

The following sutudy was made aiming at creating a means that is effective as a countermeasure for handling a pandemic of a type A influenza virus.

1. Methods and Materials
(1) Viruses

The following influenza viruses were used in this study. A/H1N1pdm: A/California/7/2009pdm (Cal09), A/Suita/1/2009pdm (Sui09); A/H1N1: A/New Caledonia/20/1999 (NC99), A/Solomon Islands/3/2006 (SI06), A/Brisbane/59/2007(Bri07). A/H3N2: A/Panama/2007/1999. A/H5N1: A/Indonesia/5/2005/PR8-IBCDC-RG2. Abbreviations for the strains are shown in the parentheses.

(2) Construction of Ab Library

Phage Ab libraries were constructed as described previously (Reference 8). Briefly, mononuclear cells from a donor born in 1947 were collected by apheresis from the equivalent of 3 L of blood before and after vaccination. They contained $8.0 \times 10^8$ B lymphocytes (before vaccination) and $1.2 \times 10^9$ B lymphocytes (after vaccination). Large combinatorial Ab libraries were constructed from them by using the phage-display method as described previously (Reference 17). The size of libraries were: before vaccination, $1.6 \times 10^9$ clones for H chain, $2.0 \times 10^9$ clones for L chain and $1.4 \times 10^{10}$ for Fab; after vaccination, $3.2 \times 10^9$ clones for H chain, $1.3 \times 10^9$ clones for L chain and $2.6 \times 10^{10}$ clones.

(3) Screening of the Library

Phages bound to virus particles were selected by a panning method as described previously (References 17 and 18). In brief, formalin-treated virus particles of Cal09 or Bri07 strains were used as Ags in the screenings. After two and three time pannings, E. coli (DH12S) cells were infected with the eluted phages and spread onto the LB plates containing 100 µg/ml ampicillin and 0.2% glucose. E. coli colonies harboring phagemid were picked up and grown in 2×YT medium containing 100 µg/ml ampicillin, 0.05% glucose and 1 mM isopropyl-β-D-thiogalactopyranoside at 30° C. overnight. During growth of E. coli, the Fab-cp3 form of Ab was secreted into the medium (Reference 19). The culture supernatants containing Fab-cp3 molecules were subjected to ELISA against H1N1 virus used as Ag in the screening and H3N2 virus. Clones that bound only to H1 were selected and subjected to further analyses.

(4) ELISA

Formalin-treated virus particles were coated onto 96 well Maxisorp immunoplates (Nunc) and Fab-cp3 Ab in the supernatant of E. coli culture was added to each well. After incubation with rabbit anti-cp3 Ab (MBL), the wells were further incubated with peroxidase-conjugated goat anti-rabbit IgG (H+L chain; MBL). Then, HRP substrate (OPD; Wako) was added to each well and color of sample was developed. After stopping peroxidase reaction by adding $H_2SO_4$, the absorbance of sample at 492 nm was measured.

(5) Sequence Analysis

The nucleotide sequences of $V_H$ fragments of isolated Ab clones were determined by using GenomeLab Dye Terminator Cycle Sequencing with Quick Start Kit (BECKMAN COULTER) and a CEQ2000 DNA Analysis System (BECKMAN COULTER). The T7ETZ (5'-TAATACGACTCAC-TATAGGG-3':SEQ ID NO:129) was used as $V_H$ sequencing primer.

(6) Virus Neutralization Test

For measurement of virus neutralizing activity, focus reduction assay was performed by using single cycling (VN) or multiple cycling (M-VN) method. Two hundred or 500 µg/ml of Fab-pp Abs or two-fold serial dilutions of serum were mixed with equal volume of 100 FFU of influenza virus, and applied to MDCK cells in 96 well plate. In VN method, after incubation with the mixture, the cells were washed with serum free MEM and cultured in MEM containing 0.4% BSA at 37° C. for 15 h. In M-VN method, after incubation, MEM containing 0.4% BSA, 5 mg/ml of acetylated trypsin, and 0.5% methyl cellulose of equal volume to the mixture was further added to the cells without removing the mixture and the cells were incubated at 37° C. for 28 h. Then the cells were fixed with ethanol and stained with PAP (peroxidase and anti-peroxidase) complex. Number of focus containing one and more cells (VN method) or four and more cells (M-VN method) per focus was counted. The results were indicated as the focus reduction rate (%) for Fab-pp Ab or the reciprocal of the highest dilution of serum to show 50% focus reduction rate for serum.

(7) Hemagglutination Inhibition (HI) Assay

The HI test was performed as described previously (Reference 20). In brief, serial dilutions of 160 µg/ml of purified Fab-PP or donor's serum in PBS were prepared. Serial dilutions of Fab-PP or serum were preincubated with 4 HA units of virus per well. 0.75% of guinea pig red blood cells in PBS were added to each well, and the plate was incubated at room temperature for 30-60 min. The results were shown as the lowest concentration (µg/ml) of Fab-pp Ab or the reciprocal of the highest dilution of serum to inhibit hemagglutination.

(8) Competition ELISA

Competition ELISA was performed by using Fab-PP form of Ab or C179 for detection of binding activity to virus particles and Fab-cp3 form of Ab as a competitor. Fab-cp3 molecules in the supernatant of E. coli culture were concentrated 20-fold before use. Formalin-inactivated virus particles were coated onto a 96 well Maxisorp immunoplate. A total of 50 µl of Fab-PP at an optimized concentration was mixed with 50 µl of 20-fold concentrated Fab-cp3 and the mixture was added to a virus-coated well. Then, peroxidase-conjugated rabbit anti streptavidine Ab was added to each well as a second Ab. When C179 at the final concentration of 0.25 µg/ml was used for detection of the binding activity to viral strain, each well was incubated with peroxidase-conjugated goat anti-mouse IgG (H+L chain; MBL) as a second Ab. Then, HRP substrate (OPD; Wako) was added to each well and color of sample was developed. After stopping peroxidase reaction by adding $H_2SO_4$, the absorbance of sample at 492 nm was measured.

(9) Preparation of K1-18 Antibody

Five kinds of Fab-pp types of 1-69 antibody (F081-007, F083-103, F083-115, F083-305 and F083-311) were each purified, injected once together with a complete Freund's adjuvant to a footpad of a mouse, and further injected once at after 11 days without an adjuvant. At 3 days after the second injection, the lymphocytes were isolated from the inguinal lymph node, and fused with myeloma cell line P3-X63AG8.653. The hybridoma was cloned, and the culture solution was screened by ELISA on various kinds of antibodies in which the above-mentioned 1-69 antibody and VH1-69 gene were not used. An antibody that binds to a plurality of antibodies using a VH1-69 gene but does not bind to an antibody which does not use VH1-69 gene was selected. The isolation of K1-18 antibody was carried out by Monoclonal Antibody Laboratory (Sapporo, Japan).

(10) Determine the Concentration of IgG Using VH 1-69 Germline Gene in Serum

Human IgG ELISA Quantitation set (Bethyl Laboratories, Inc) was used, with slight modification. K1-18 Ab for detection of IgG using VH 1-69 germline gene and affinity purified Human IgG coating antibody for standard curve were coated onto 96 well Maxisorp immuonoplate. Serum and Human reference serum (for standard curve) was added to the assigned well. After incubation with HRP conjugated Human IgG Detection Antibody, TMB substrate was added to each well. Peroxidase reaction was stopped by adding $H_2SO_4$ and the absorbance of sample at 450 nm was measured. The concentration of IgG bound to K1-18 Ab was calculated from standard curve of human reference serum.

(11) Virus-Neutralizing Activity of Serum in the Presence of K1-18 Ab

Virus neutralization test described above was modified. In brief, serum treated with RDE was diluted at 1:10 or 1:20 in serum-free medium and mixed with equal volume of 800 or 1,600 μg/ml of K1-18 Ab. After incubation, two-fold serial dilutions of the mixture were mixed with equal volume of 100 FFU of influenza virus, and applied to MDCK cells in 96 well plate. After incubation, the cells were fixed with ethanol and stained with PAP (peroxidase and anti-peroxidase) complex. The reciprocal of the highest dilution of serum to show 50% focus reduction rate was indicated as virus neutralizing activity.

2. Results (1) Two Types of Virus-Neutralizing Abs with Different Characteristics We examined the total repertoire of Abs induced by vaccination with S-IOV. The blood donor in this study was born in 1947. He suffered from influenza several times in his childhood (possibly by H1N1 and H2N2) and finally in 1968 (probably by H3N2). During 41 years afterwards, he did not suffer from influenza at all, and moreover, he had never been vaccinated against influenza. The schedule of vaccination and blood collection was indicated in FIG. 4. This operation was performed for the period from the end of October until the middle of December in 2009 and the examinee did not have an opportunity of natural infection with S-IOV. By using B lymphocytes collected before and after vaccination, two large Ab libraries were constructed and subjected to screenings by panning with pandemic H1N1 (A/California/2009pdm) and with seasonal H1N1 (A/Brisbane/2007) virus particles. After the second and the third rounds of panning with the viruses, 120 clones were isolated. The clones that bound to the H1N1 virus particle that had been used for screenings were further analyzed. The clones that bound to both H1N1 and H3N2 at equally intense strength were excluded since it is likely they are anti-NP Abs (Reference 8). Among 240 clones isolated in respective screenings, the number of clones that have been judged to be anti-HA Abs is as follows: screening 1 (library after vaccination, panning with pandemic virus), 105 clones; screening 2 (library before vaccination, panning with pandemic virus), 3 clones; screening 3 (library after vaccination, panning with seasonal virus), 58 clones; screening 4 (library before vaccination, panning with seasonal virus), 16 clones. $V_H$ nucleotide sequences of all these clones were determined. Comparison of the amino acid sequences revealed that these 182 clones were composed of 96 unique monoclonal Abs (mAbs). Based on sequence similarities of $V_H$ fragments, in particular the comparison of complementarity-determining region 3 (CDR3) sequences, the 96 clones were classified into 63 groups. The amino acid sequence of $V_H$ fragment and the nucleotide sequence of CDR3 of all the clones are available in FIG. 5.

Figure 1:
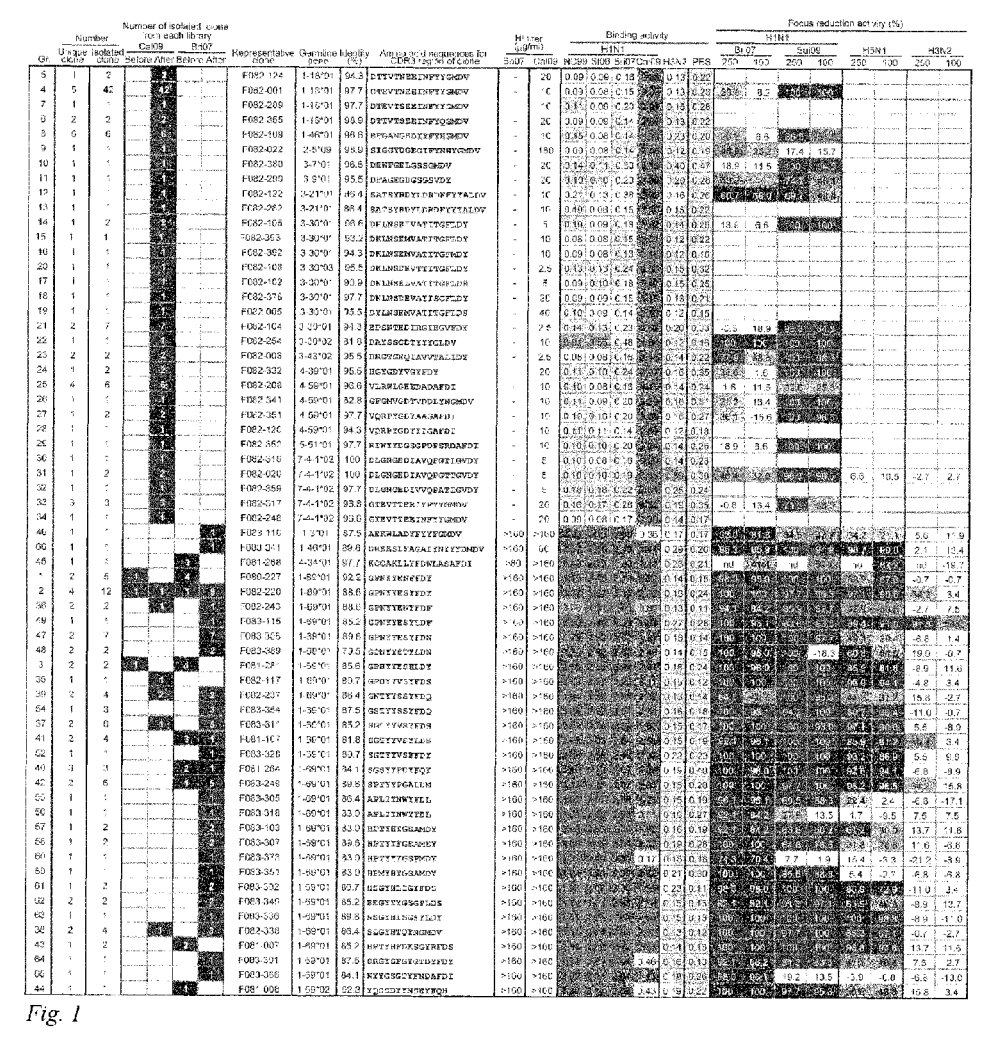

Using representative clones of the 63 groups, the following activities were examined: the binding activity to HAs; hemagglutination inhibition (HI) activity; the virus-neutralizing activity (Reference 9). As shown in FIG. 1, they were classified into two types without any exceptional clone. Clones classified into the first type bind only to the pandemic H1N1 not to the seasonal H1N1. All of them show HI activity. They were isolated only from screening 1. Clones classified into the second type bind not only to the pandemic H1N1 but also to all of the seasonal H1N1s. While they do not show HI activity, most of them neutralize not only H1N1 viruses but also H5N1 virus. Judging from low frequency of mutation such as 0 to 5%, majority of the first type clones should be the products by B cells that have been newly induced through vaccination. On the other hand, all the clones except for few in the second type should correspond to the products by long-lived memory B cells that had been established before vaccination, judging from high frequency of mutation such as 10 to 15%. Furthermore, they utilize 1-69 $V_H$ gene except for three clones.

Of 105 clones isolated from screening 1, 98 were the first type and only 7 were the second type. Since the second type clones can bind to not only HA of the seasonal virus but also that of the pandemic virus, this low number means that the number of cells that produced the second type Abs was much lower than that of the first type Abs in the blood. As the first type Ab, 98 clones were isolated and classified into 31 groups. Of 31 groups, only one clone was isolated in 19 groups, and 2 clones were isolated in 7 groups. Similarly, as the second type Ab, 85 clones were isolated and classified into 32 groups. Of 32 groups, only one clone was isolated in 14 groups, and 2 clones were isolated in 8 groups. Taking account of the Poisson distribution, these observations suggested that there should be more clones that we have overlooked in this screening. However, it is unlikely that we have specifically overlooked the clones whose characteristics are very different from those listed in FIG. 1.

(2) Newly Appearing Abs After Vaccination

Since virtually all the first type Abs showed HI activity, it is likely that their epitopes are located in the surrounding region of a sialic acid-binding pocket. In order to systematically examine the relative position of the epitopes recognized by these clones we adopted the competition method which we had used in the previous study (Reference 10). While respective mAbs are initially prepared as Fab-cp3 form after the screening of libraries, they can be easily changed to Fab-PP (P denotes a single Fc-binding domain of protein A) form in our vector construct (Reference 11). If the epitope recognized by clone A is overlapped with that by clone B, the binding of Fab-PP form of clone A to HA is largely disturbed by the presence of a large amount of Fab-cp3 form of clone B. Based on this principle, the competition study was performed using 17 clones selected from the first type Abs listed in FIG. 1. As the results are shown in FIG. 2, 14 clones among 17 well competed against one another for the binding to HA. In the case of three clones, F082-317, F082-254 and F082-022, the degree of disturbance for the binding was low. These observations are consistent with other data. Only F082-022 showed very low HI activity (titer 160 μg/ml). F082-254 binds to HA of not only pandemic virus but also seasonal virus and neutralizes both viruses. Furthermore, high frequency of mutation such as 18% was observed in this clone. In the case of F082-317, the binding activity to HA is high but the neutralizing activity is relatively low.

Based on these observations we concluded that the sialic acid-binding pocket and its surrounding regions on HA are immunogenically very potent, and virtually all the B cells whose growth is newly induced and expanded by vaccination produce Abs that recognize these regions. In addition, when even formalin-treated virus particles that are not alive are used as vaccine, B cells producing Abs that are able to bind to HA but not able to neutralize virus are not induced at a substantial level. The second conclusion suggested that the non-neutralizing epitope on HA, even if it exists, is immunologically impotent.

(3) Abs Encoded By Long-Lived Memory B Cells

While the second type clones are classified into 32 groups, they utilized 1-69 $V_H$ gene except for three clones. Furthermore, majority of them are able to neutralize not only all of H1N1 viruses but also H5N1 virus. These observations suggested that the epitopes recognized by these clones should be closely located at that recognized by C179 as shown by several groups (References 12 and 13). Then, we examined whether the binding of C179 to HA is really disturbed by presence of large excess of Fab-cp3 form of these clones. As the results are shown in FIG. 3, all of the clones including three that did not utilize 1-69 $V_H$ gene disturbed the binding of C179 to HA. Thus, the second type clones should bind to the membrane-proximal stem of HA in the same or similar way as other Abs using 1-69 $V_H$ gene (1-69Abs), such as CR6261 and F10, already described by other groups (References 12 and 13). FIG. 3 also indicated that four clones, F081-268, F082-243, F082-237, and F083-373, showed weaker disturbance activity than the others. The data shown in FIG. 1 indicated that F081-268 showed intense HA-binding activity but the neutralizing activity was weak. The other three clones showed relatively weak binding and neutralizing activities. Thus, while all of the epitopes recognized by the second type Abs are not exactly the same as that by C179, we did not find any clone that binds to the epitope totally different from that recognized by C179. This suggested that this epitope has been shared and stably kept among group 1 viruses. Even if the immunogenicity of this epitope is weak, once humans acquired B cells that produce Abs that recognize this epitope, they could have been kept in their bodies as memory cells for a long time and have become major players against group 1 viruses. Interestingly, one clone F083-115-1 that utilized 1-69 $V_H$ gene is able to neutralize even H3N2 virus.

Eighty-four clones isolated as the second type Abs were composed of 49 unique clones. They were further classified into 32 groups. Although we assumed that respective groups may correspond to B cells that had been matured independently of one another during differentiation of B cells, some of the clones that were classified into different groups in FIG. 1 may have been derived from the same B cells. Even if this is the case, the list of clones summarized in FIG. 1 indicated that more than 10 B cells using 1-69 $V_H$ gene had been independently established in the donor's body probably when he was young. While 16 anti HA clones were isolated from screening 4 (library before vaccination, panning with seasonal virus), there was no clone that binds to HA of seasonal H1N1 virus but not to that of pandemic virus. All of them were the second type Abs. Since the library used in this screening was constructed from B cells before vaccination, expansion of the first type B cells through vaccination did not give any influence on the characteristics of clones isolated from screening 4. If there were B cells that produce Abs that bind to the globular head of HA in seasonal H1N1 viruses at a substantial level, we should have obtained such clones. The strategy adopted in this study were utilized in analyses of repertoire of neutralizing Abs against H3N2 viruses in three blood donors in our previous study (References 8 and 10). Although vaccination step was not included in the previous study, most of the Abs isolated bound to the globular head of HA (References 10 and 14). Thus, we concluded that the 1-69Abs that are able to neutralize all of group 1 viruses should have been major players against group 1 influenza A viruses in the donor's body for a long time.

(4) Presence of Abs Secreted Into the Serum

Figure 4:
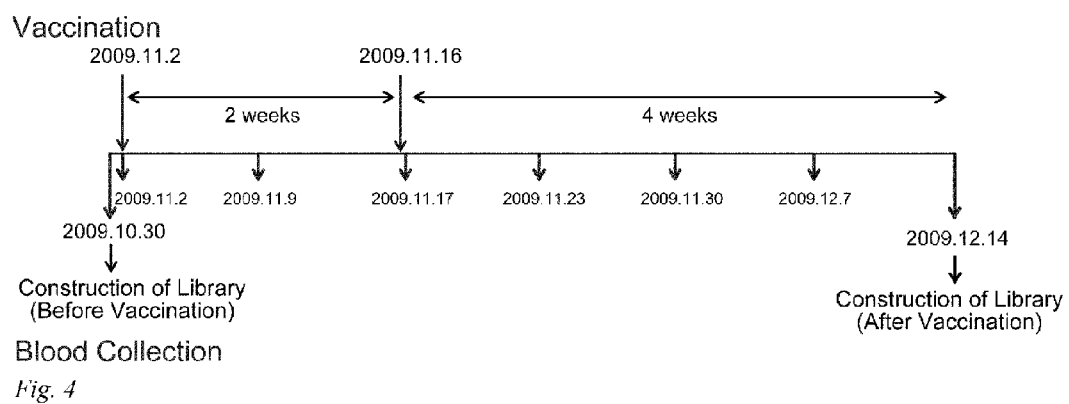
FIG. 4 Schedule of vaccination and blood collection. In 2009, a donor born in 1947 was vaccinated with A/California/7/2009 pandemic vaccine strain two times (on November 2 and 16). Blood was collected from this donor two times before vaccination (on October 30 and November 2), a time after 1st vaccination (on November 9) and 5 times after 2nd vaccination (on November 17, 23, 30, December 7, and 14). Large phage Ab libraries were prepared from blood collected on October 30 (before vaccination) and December 14 (after vaccination), respectively.

Two biological activities, HI activity and virus-neutralizing activity, against three viral strains, H1N1 pandemic virus, seasonal H1N1 virus and H5N1 virus, were measured using eight samples of sera collected from the examinee at different date as shown in FIG. 4.

As indicated in FIG. 6, in the case of HI, the activity against seasonal H1N1 and H5N1 viruses was not detected in all the sera. Against H1N1 pandemic virus, HI activity started to appear two weeks after the first vaccination. In the case of virus-neutralizing activity measured by standard focus reduction assay, the activity against H1N1 pandemic virus already started to increase one week after vaccination and reached to plateau two weeks after vaccination. Against seasonal H1N1 virus, virus-neutralizing activity was detected even before vaccination and increased one week after vaccination. Against H5N1 virus, virus-neutralizing activity was not detected by the standard focus-reduction assay (Reference 9) but detected by more sensitive method.

Since virus-neutralizing activity against H5N1 virus should be derived from the set of Abs which had been originally generated against H1N1 and probably H2N2 viruses in the examinee's body and were listed as the second type in FIG. 1, the difference observed between seasonal H1N1 virus and H5N1 virus may correspond to difference in the strength of activity, that is, the activity against seasonal H1N1 virus is several times intenseer than that against H5N1 virus. It should be noteworthy that virus-neutralizing activity against seasonal H1N1 was observed at the detectable level even before vaccination.

Figure 8:
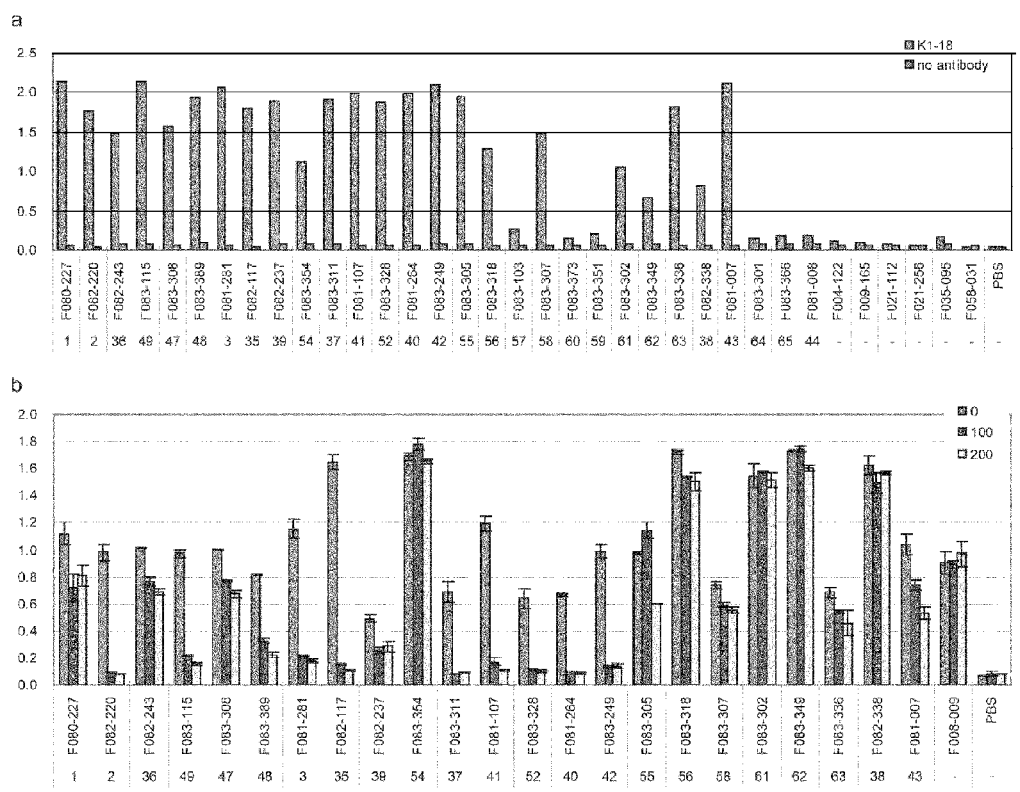
FIG. 8 The characteristics of K1-18 antibody. (a) The binding activity of K1-18 antibody against antibodies using VH1-69 gene. The binding activity of K1-18 antibody against antibodies using VH1-69 gene was measured by ELISA. F004-122, F009-165, F021-112, F021-256, F035-095 and F058-031 do not use a VH1-69 gene. The group numbers are indicated under the clone names. (b) The binding activities of the respective antibodies against virus particles in the presence of K1-18. The binding activities of the antibodies using VH1-69 gene against Bri07 virus particles were measured by ELISA in the presence of K1-18 antibody (100 or 200 μg/ml). F008-009 is used as not an anti-HA antibody but a negative control. The group numbers are indicated under the clone names. The experiments were conducted with duplication, and a standard deviation is indicated by an error bar.

In order to prove that 1-69Abs are really responsible for neutralizing H1N1 pandemic virus, seasonal H1N1 virus and H5N1 virus, we decided to prepare mAb that can specifically bind to 1-69Abs, that is anti-idiotypic Ab, and hopefully inhibit the binding of 1-69Ab to HA. We expected that the region including two amino acids, isoleucine at the 53rd residue and phenylalanine at the 54th residue, in $V_H$ domain should be immunogenic in mice since presence of two hydrophobic residues in CDR2 is very unique, and is found only in 1-69Ab of human. We expected that an anti-idiotypic Ab is able to inhibit the binding of 1-69Ab to HA since it has been shown that these two amino acids are directly involved in the Ab/HA interaction (References 12 and 13). We isolated mAb K1-18 that can bind to more than 80% of 1-69Abs listed in FIG. 1. For half of the 1-69Abs, the binding to HA is inhibited by K1-18. See "Methods and FIG. 8 for the details.

Using K1-18 as probe, amount of IgG form of 1-69Ab in serum was measured. The results indicated that it was present at the concentration of 4.58 µg/ml in the serum of October 30 (before vaccination) and increased after vaccination to the concentration of 11.24 µg/ml in the serum of December 14 (after vaccination). Virus-neutralizing activity against pandemic and seasonal H1N1 viruses were measured under presence of K1-18. In the case of H1N1 pandemic virus, K1-18 definitely inhibited the neutralizing activity as indicated in FIG. 7. Against seasonal H1N1 virus, the inhibition was clearly observed although not perfectly. Thus, we concluded that 1-69Abs were really present in the sera and functioned in neutralization of H1N1 viruses. Furthermore, the data in FIG. 7 suggested that when two types of functionally different Abs co-exist, the first type prevents HA/receptor interaction and the second type prevents low-pH-induced conformational change of HA, the virus-neutralizing activity synergistically increases.

3. Perspective

In the study reported before, the research group of the present inventors analyzed the neutralization antibody repertoires of three humans through isolation of large amounts of anti-HA antibodies against 12 kinds of different H3 strains that were isolated in a period from 1968 to 2004 (Reference Documents 8, 10 and 14). Most of the antibodies isolated from two donors who were born in 1960 and 1944 were classified into three groups having different strain specificities (specificities to strains in a period from 1968 to 1973, specificities to strains in a period from 1977 to 1993, and specificities to strains in a period from 1997 to 2003). Five sites of A, B, C, D and E that are positioned on the head part of HA were isolated as neutralizing epitopes, whereas many of the clones that neutralizes the strains in a period from 1977 to 1993 bonded to the site C. The clones that were isolated from the third donor born in 1974 can be classified into four types. Type 1 strongly bound to the 1973 strain, and the strain specificity was narrow. Type 2 bound to the HAs of the strains in a period from 1997 to 2003. The other two types were antibodies that broadly neutralize the strains. One was an antibody that neutralizes all kinds of H3N2, and the other was an antibody that neutralizes not only H3 but also group 1 viruses including H1, H2 and H5. After a set of B cells producing Abs that can neutralize the viruses are generated by immunization through infection and/or vaccination, they will take various courses under further stimulation with the antigens (Ags). Some B cells disappear but others remain as memory cells. Furthermore, there should be long-lived memory cells and short-lived memory cells. Humans who experience an outbreak of flu almost every year should have opportunities to be infected by novel influenza viruses that have drifted away from previous virus. Some memory cells produce Abs that are able to neutralize the novel viruses but others produce Abs that cannot neutralize them. They would be selected through presence or absence of stimulation with the Ags. According to this hypothesis the stability of the epitope would greatly affect the fate of memory B cells. The present study indicated that only the cells producing 1-69Abs which can neutralize all the group 1 viruses remained as memory cells. In this experiment we analyzed the person who had experience of suffering from influenza disease in their youth but never suffered from this disease afterwards. Since the donor had not received any influenza vaccine until then, it is considered that the antibody repertoire produced in the body of the donor was produced by only an effect of infection with a living virus. An antibody repertoire that is formed in the body of a human that has received a vaccine many times with a formalin-treated virus would not indicate a simple tendency as shown in this study. Further, although only one person was analyzed in this study, it seemed likely that any human is able to generate 1-69Abs that can broadly neutralize group 1 viruses since only 1-69 $V_H$ gene is required for producing a broadly neutralizing Ab without participation of $V_L$ domain in forming the Ag-binding site, and furthermore, the requirements of CDR3 sequence in $V_H$ for binding to HA stem appeared to be limited. While further experiments are required to examine whether Abs produced in the type 2 clones are intense enough for preventing infection with future pandemic caused by highly pathogenic avian influenza (HPAI) H5N1 virus, we may expect that presence of type 2 clones as memory cells could be helpful for preventing expansion of the pandemic viruses in their bodies. Thus, we propose that the strategy for protection against the H5N1 pandemic should be designed according to the immunological carrier of respective persons. Presence of anti HA Abs utilizing 1-69 $V_H$ gene could be a useful indicator for the judgment and anti idiotypic Abs against 1-69Abs could be the reagent.

INDUSTRIAL APPLICABILITY

The present invention is useful as a countermeasure for handling a pandemic of a type A influenza virus. By utilizing the present invention, it becomes possible to take a reasonable and effective countermeasure for handling the pandemic.

The present invention will not be limited to the description of the embodiments and examples of the present invention. Various modifications readily made by those skilled in the art are also included in the present invention, without departing from the scope of claims.

The contents of the articles, unexamined patent publications, and patent applications specified herein are hereby incorporated herein by reference.

REFERENCES

1. Skehel, J. J. & Wiley, D. C. Receptor binding and membrane fusion in virus entry: the influenza hemagglutinin. *Ann. Rev. Biochem.* 69, 531-569 (2000).
2. Knossow, M. et al. Mechanism of neutralization of onfluenza virus infectivity by antibodies. *Virology* 302, 294-298 (2002).
3. Okuno, Y., Isegawa, Y., Sasao, F. & Ueda, S. A common neutralizing epitope conserved between the hemagglutinins of influenza A virus H1 and H2 strains. *J. Virol.* 67, 2552-2558 (1993).
4. Fraser, C. et al. Pandemic potential of a strain of influenza A (H1N1): early findings. *Science* 324, 1557-1561 (2009).
5. Hancock, K. et al. Cross-reactive antibody responses to the 2009 pandemic H1N1 influenza virus. *N. Engl. J. Med.* 361, 1945-1952 (2009).
6. Wrammert, J. et al. Broadly cross-reactive antibodies dominate the human B cell response against 2009 pandemic H1N1 influenza virus infection. *J. Exp. Med.* 208, 181-193 (2011).
7. Li, G. M. et al. Pandemic H1N1 influenza vaccine induces a recall response in humans that favors broadly cross-reactive memory B cells. *Proc. Natl. Acad. Sci.* 109, 9047-9052 (2012).
8. Okada, J. et al. Monoclonal antibodies in man that neutralized H3N2 influenza viruses were classified in to three groups with distinct strain specificity: 1968-1973, 1977-1993 and 1997-2003. *Virology* 397, 322-330 (2010).
9. Okuno, Y. et al. Rapid focus reduction neutralization test of influenza A and B viruses in microtiter system. *J. Clin. Microbiol.* 28, 1308-13131 (1990).
10. Ohshima, N. et al. Naturally occurring antibodies in humans can neutralize a variety of influenza viral strains, including H3, H1, H2, and H5. *J. Virol.* 85, 11048-11057 (2011).
11. Ito, W. & Kurosawa, Y. Development of an artificial antibody system with multiple valency using an Fv fragment fused to a fragment of protein A. *J. Biol. Chem.* 268, 20668-20675 (1993).
12. Sui, J. et al. Structural and functional bases for broad-spectrum neutralization of avian and human influenza A viruses. *Nat. Struc. Mol. Biol.* 16, 265-273 (2009).
13. Ekiert, D. C. et al. Antibody recognition of a highly conserved influenza virus epitope. *Science* 324, 246-251 (2009).
14. Okada, J. et al. Localization of epitopes recognized by monoclonal antibodies that neutralized the H3N2 influenza viruses in man. *J. Gen. Virol.* 92, 326-335 (2011).

[Sequence List Free Text]

SEQ ID NO:129: explanation of artificial sequence: primer T7ETZ

The invention claimed is:

1. A method of determining resistance to an infection by a Group 1 type A influenza virus by using the presence of an antibody using VH1-69 gene in a biological sample derived from a subject, comprising the following steps (1) to (3):

(1) a step of bringing a biological sample of a subject that has received an influenza vaccine into contact with an anti-ideotype antibody that specifically recognizes an antibody using VH1-69 gene derived antibodies that are able to bind hemagglutinin (HA) that is shared among Group 1 type A influenza viruses;

(2) a step of detecting a generated immune complex;

(3) a step of determining the intensity of the resistance to an infection by a Group 1 type A influenza virus based on the detection result in the step (2), wherein the amount of the detected immune complex serves as an indicator of the intensity of the resistance to an infection by the Group 1 type A influenza virus.

2. The method according to claim 1, further comprising the following step:
   (4) a step of detecting an immune complex generated by bringing a biological sample of a subject before receiving the influenza vaccine into contact with an anti-ideotype antibody that recognizes an antibody using VH1-69 gene, comparing the amount of the immune complex with the amount of the immune complex detected in the step (2), and determining the intensity of the resistance based on the result of the comparison.

3. The method according to claim 1, wherein the biological sample is a blood sample.

4. The method according to claim 1, wherein the Group 1 type A influenza virus is one or more viruses selected from the group consisting of H1N1, H1N2, H2N2, H5N1, H5N2, and H6N1.

5. The method according to claim 1, wherein the Group 1 type A influenza virus is one or more viruses selected from the group consisting of H1N1, H2N2, and H5N1.

6. The method according to claim 1, wherein the Group 1 type A influenza virus is one or more viruses selected from the group consisting of H1N1, H1N2, H2N2, H5N1 and H5N2.

* * * * *

SEQUENCE LISTING

<160> NUMBER OF SEQ ID NOS: 129

<210> SEQ ID NO 1
<211> LENGTH: 17
<212> TYPE: PRT
<213> ORGANISM: Homo sapience

<400> SEQUENCE: 1

Asp Thr Thr Val Thr Asn Glu Glu Ile Asn Phe Tyr Tyr Gly Met Asp
1               5                   10                  15

Val

<210> SEQ ID NO 2
<211> LENGTH: 17
<212> TYPE: PRT
<213> ORGANISM: Homo sapience

<400> SEQUENCE: 2

Asp Thr Glu Val Thr Asn Glu Glu Ile Asn Phe Tyr Tyr Gly Met Asp
1               5                   10                  15

Val

<210> SEQ ID NO 3
<211> LENGTH: 17
<212> TYPE: PRT
<213> ORGANISM: Homo sapience

<400> SEQUENCE: 3

Asp Thr Glu Val Thr Ser Glu Glu Ile Asn Phe Tyr Tyr Gly Met Asp
1               5                   10                  15

Val

<210> SEQ ID NO 4
<211> LENGTH: 17
<212> TYPE: PRT
<213> ORGANISM: Homo sapience

<400> SEQUENCE: 4

Asp Thr Thr Val Thr Ser Glu Glu Ile Asn Phe Tyr Gln Gly Met Asp
1               5                   10                  15

Val

<210> SEQ ID NO 5
<211> LENGTH: 17
<212> TYPE: PRT
<213> ORGANISM: Homo sapience

<400> SEQUENCE: 5

Glu Phe Gly Ala Asn Gly Glu Asp Ile Tyr Phe Tyr His Gly Met Asp
1               5                   10                  15

Val

<210> SEQ ID NO 6
<211> LENGTH: 19
<212> TYPE: PRT
<213> ORGANISM: Homo sapience

<400> SEQUENCE: 6

Ser Ile Gly Gly Tyr Asp Gly Glu Gly Ile Phe Tyr Asn His Tyr Gly
1               5                   10                  15

Met Asp Val

<210> SEQ ID NO 7
<211> LENGTH: 14
<212> TYPE: PRT
<213> ORGANISM: Homo sapience

<400> SEQUENCE: 7

Asp Glu Trp Phe Gly Glu Leu Gly Ser Ser Gly Met Asp Val
1               5                   10

<210> SEQ ID NO 8
<211> LENGTH: 14
<212> TYPE: PRT
<213> ORGANISM: Homo sapience

<400> SEQUENCE: 8

Asp Phe Ala Gly Glu Gly His Gly Ser Gly Ser Val Asp Tyr
1               5                   10

<210> SEQ ID NO 9
<211> LENGTH: 20
<212> TYPE: PRT
<213> ORGANISM: Homo sapience

<400> SEQUENCE: 9

Ser Ala Thr Ser Tyr Arg Asp Tyr Leu Asp Arg Asp Phe Phe Tyr
1               5                   10                  15

Ala Leu Asp Val
            20

<210> SEQ ID NO 10
<211> LENGTH: 20
<212> TYPE: PRT
<213> ORGANISM: Homo sapience

<400> SEQUENCE: 10

Ser Ala Thr Ser Tyr Arg Asp Tyr Leu Asp Arg Asp Phe Tyr Tyr
1               5                   10                  15

Ala Leu Asp Val
            20

<210> SEQ ID NO 11
<211> LENGTH: 17
<212> TYPE: PRT
<213> ORGANISM: Homo sapience

<400> SEQUENCE: 11

Asp His Leu Asn Ser Glu Ile Val Ala Thr Ile Thr Gly Phe Leu Asp
1               5                   10                  15

Tyr

<210> SEQ ID NO 12
<211> LENGTH: 17
<212> TYPE: PRT
<213> ORGANISM: Homo sapience

<400> SEQUENCE: 12

Asp Lys Leu Asn Ser Glu Met Val Ala Thr Ile Thr Gly Phe Leu Asp
1               5                   10                  15

Tyr

<210> SEQ ID NO 13

```
<211> LENGTH: 17
<212> TYPE: PRT
<213> ORGANISM: Homo sapience

<400> SEQUENCE: 13

Asp Lys Leu Asn Ser Glu Met Val Ala Thr Ile Thr Gly Phe Met Asp
1               5                   10                  15

Tyr

<210> SEQ ID NO 14
<211> LENGTH: 17
<212> TYPE: PRT
<213> ORGANISM: Homo sapience

<400> SEQUENCE: 14

Asp Lys Leu Asn Ser Asp Glu Val Thr Thr Ile Thr Gly Phe Leu Asp
1               5                   10                  15

Tyr

<210> SEQ ID NO 15
<211> LENGTH: 17
<212> TYPE: PRT
<213> ORGANISM: Homo sapience

<400> SEQUENCE: 15

Asp Asn Leu Asn Ser Glu Leu Val Ala Thr Ile Thr Gly Phe Leu Asp
1               5                   10                  15

His

<210> SEQ ID NO 16
<211> LENGTH: 17
<212> TYPE: PRT
<213> ORGANISM: Homo sapience

<400> SEQUENCE: 16

Asp Asn Leu Asn Ser Asp Glu Val Ala Thr Ile Ser Gly Phe Leu Asp
1               5                   10                  15

Tyr

<210> SEQ ID NO 17
<211> LENGTH: 17
<212> TYPE: PRT
<213> ORGANISM: Homo sapience

<400> SEQUENCE: 17

Asp Tyr Leu Asn Ser Glu Met Val Ala Thr Ile Thr Gly Phe Leu Asp
1               5                   10                  15

Ser

<210> SEQ ID NO 18
<211> LENGTH: 17
<212> TYPE: PRT
<213> ORGANISM: Homo sapience

<400> SEQUENCE: 18

Glu Pro Ser Asn Thr Glu Asp Ile Arg Gly Ile Glu Gly Val Phe Asp
1               5                   10                  15

Tyr

<210> SEQ ID NO 19
<211> LENGTH: 15
```

```
<212> TYPE: PRT
<213> ORGANISM: Homo sapience

<400> SEQUENCE: 19

Asp Ala Tyr Ser Ser Gly Asp Thr Tyr Tyr Tyr Gly Leu Asp Val
1               5                   10                  15

<210> SEQ ID NO 20
<211> LENGTH: 17
<212> TYPE: PRT
<213> ORGANISM: Homo sapience

<400> SEQUENCE: 20

Asp Arg Gly Thr Gly Glu Gln Ile Ala Val Val Thr Ala Leu Ile Asp
1               5                   10                  15

Tyr

<210> SEQ ID NO 21
<211> LENGTH: 12
<212> TYPE: PRT
<213> ORGANISM: Homo sapience

<400> SEQUENCE: 21

His Gly Tyr Gly Asp Tyr Val Gly Tyr Phe Asp Tyr
1               5                   10

<210> SEQ ID NO 22
<211> LENGTH: 15
<212> TYPE: PRT
<213> ORGANISM: Homo sapience

<400> SEQUENCE: 22

Val Leu Arg Trp Leu Gly Glu Glu Asp Ala Asp Ala Phe Asp Ile
1               5                   10                  15

<210> SEQ ID NO 23
<211> LENGTH: 18
<212> TYPE: PRT
<213> ORGANISM: Homo sapience

<400> SEQUENCE: 23

Gly Phe Gly Met Val Gly Asp Thr Val Asp Asp Leu Tyr Asn Gly Met
1               5                   10                  15

Asp Val

<210> SEQ ID NO 24
<211> LENGTH: 15
<212> TYPE: PRT
<213> ORGANISM: Homo sapience

<400> SEQUENCE: 24

Val Gln Arg Pro Tyr Gly Asp Tyr Ala Ala Gly Ala Phe Asp Ile
1               5                   10                  15

<210> SEQ ID NO 25
<211> LENGTH: 15
<212> TYPE: PRT
<213> ORGANISM: Homo sapience

<400> SEQUENCE: 25

Val Gln Arg Pro Tyr Gly Asp Tyr Ile Thr Gly Ala Phe Asp Ile
1               5                   10                  15
```

```
<210> SEQ ID NO 26
<211> LENGTH: 19
<212> TYPE: PRT
<213> ORGANISM: Homo sapience

<400> SEQUENCE: 26

Arg Thr Trp Tyr Tyr Asp Gly Ser Gly Pro Asp Pro Ser Arg Asp Ala
1               5                   10                  15
Phe Asp Ile

<210> SEQ ID NO 27
<211> LENGTH: 19
<212> TYPE: PRT
<213> ORGANISM: Homo sapience

<400> SEQUENCE: 27

Asp Leu Gly Asn Gly Glu Asp Ile Ala Val Gln Pro Gly Thr Ile Gly
1               5                   10                  15
Val Asp Tyr

<210> SEQ ID NO 28
<211> LENGTH: 19
<212> TYPE: PRT
<213> ORGANISM: Homo sapience

<400> SEQUENCE: 28

Asp Leu Gly Asn Gly Glu Asp Ile Ala Val Gln Pro Gly Thr Thr Gly
1               5                   10                  15
Val Asp Tyr

<210> SEQ ID NO 29
<211> LENGTH: 19
<212> TYPE: PRT
<213> ORGANISM: Homo sapience

<400> SEQUENCE: 29

Asp Leu Gly Asn Gly Glu Asp Ile Val Val Gln Pro Ala Thr Ile Gly
1               5                   10                  15
Val Asp Tyr

<210> SEQ ID NO 30
<211> LENGTH: 17
<212> TYPE: PRT
<213> ORGANISM: Homo sapience

<400> SEQUENCE: 30

Gly Thr Glu Val Thr Thr Glu Glu Ile Tyr Phe Tyr Tyr Gly Met Asp
1               5                   10                  15
Val

<210> SEQ ID NO 31
<211> LENGTH: 17
<212> TYPE: PRT
<213> ORGANISM: Homo sapience

<400> SEQUENCE: 31

Gly Thr Glu Val Thr Thr Glu Glu Ile Asn Phe Tyr Tyr Gly Met Asp
1               5                   10                  15
Val

<210> SEQ ID NO 32
```

```
<211> LENGTH: 16
<212> TYPE: PRT
<213> ORGANISM: Homo sapience

<400> SEQUENCE: 32

Ala Glu Lys Trp Leu Ala Asp Tyr Phe Tyr Tyr Phe Gly Met Asp Val
1               5                   10                  15

<210> SEQ ID NO 33
<211> LENGTH: 20
<212> TYPE: PRT
<213> ORGANISM: Homo sapience

<400> SEQUENCE: 33

Asp Arg Glu Glu Ser Leu Phe Ala Gly Ala Ile Tyr Asn Tyr Tyr Tyr
1               5                   10                  15

Asp Met Asp Val
            20

<210> SEQ ID NO 34
<211> LENGTH: 18
<212> TYPE: PRT
<213> ORGANISM: Homo sapience

<400> SEQUENCE: 34

Lys Gly Gly Ala Lys Leu Leu Tyr Phe Asp Trp Leu Ala Ser Ala Phe
1               5                   10                  15

Asp Ile

<210> SEQ ID NO 35
<211> LENGTH: 11
<212> TYPE: PRT
<213> ORGANISM: Homo sapience

<400> SEQUENCE: 35

Gly Pro Asn Tyr Tyr Glu Asn Phe Phe Asp Tyr
1               5                   10

<210> SEQ ID NO 36
<211> LENGTH: 11
<212> TYPE: PRT
<213> ORGANISM: Homo sapience

<400> SEQUENCE: 36

Gly Pro Asn Tyr Tyr Glu Ser Tyr Phe Asp Tyr
1               5                   10

<210> SEQ ID NO 37
<211> LENGTH: 11
<212> TYPE: PRT
<213> ORGANISM: Homo sapience

<400> SEQUENCE: 37

Gly Pro Asn Tyr Tyr Glu Asn Tyr Phe Asp Phe
1               5                   10

<210> SEQ ID NO 38
<211> LENGTH: 11
<212> TYPE: PRT
<213> ORGANISM: Homo sapience

<400> SEQUENCE: 38

Gly Pro Asn Tyr Tyr Glu Ser Tyr Leu Asp Phe
1               5                   10
```

```
<210> SEQ ID NO 39
<211> LENGTH: 11
<212> TYPE: PRT
<213> ORGANISM: Homo sapience

<400> SEQUENCE: 39

Gly Pro Asn Tyr Phe Glu Ser Tyr Phe Asp Asn
1               5                   10

<210> SEQ ID NO 40
<211> LENGTH: 11
<212> TYPE: PRT
<213> ORGANISM: Homo sapience

<400> SEQUENCE: 40

Gly Pro Asn Tyr Tyr Glu Thr Tyr Leu Asp Asn
1               5                   10

<210> SEQ ID NO 41
<211> LENGTH: 11
<212> TYPE: PRT
<213> ORGANISM: Homo sapience

<400> SEQUENCE: 41

Gly Pro His Tyr Tyr Glu Ser His Leu Asp Tyr
1               5                   10

<210> SEQ ID NO 42
<211> LENGTH: 11
<212> TYPE: PRT
<213> ORGANISM: Homo sapience

<400> SEQUENCE: 42

Gly Pro His Tyr Tyr Val Ser Tyr Phe Asp Ser
1               5                   10

<210> SEQ ID NO 43
<211> LENGTH: 11
<212> TYPE: PRT
<213> ORGANISM: Homo sapience

<400> SEQUENCE: 43

Gly Asn Thr Tyr Tyr Ser Ser Tyr Phe Asp Gln
1               5                   10

<210> SEQ ID NO 44
<211> LENGTH: 11
<212> TYPE: PRT
<213> ORGANISM: Homo sapience

<400> SEQUENCE: 44

Gly Ser Thr Tyr Tyr Ser Ser Tyr Phe Asp Gln
1               5                   10

<210> SEQ ID NO 45
<211> LENGTH: 11
<212> TYPE: PRT
<213> ORGANISM: Homo sapience

<400> SEQUENCE: 45

Ser Gly Thr Tyr Tyr Val Ser Tyr Phe Asp Ser
1               5                   10
```

<210> SEQ ID NO 46
<211> LENGTH: 11
<212> TYPE: PRT
<213> ORGANISM: Homo sapience

<400> SEQUENCE: 46

Ser Gly Thr Tyr Tyr Val Ser Tyr Leu Asp Ser
1               5                   10

<210> SEQ ID NO 47
<211> LENGTH: 11
<212> TYPE: PRT
<213> ORGANISM: Homo sapience

<400> SEQUENCE: 47

Ser Gly Thr Tyr Tyr Val Ser Phe Phe Asp Tyr
1               5                   10

<210> SEQ ID NO 48
<211> LENGTH: 11
<212> TYPE: PRT
<213> ORGANISM: Homo sapience

<400> SEQUENCE: 48

Ser Gly Ser Tyr Tyr Pro Asp Tyr Phe Gln Tyr
1               5                   10

<210> SEQ ID NO 49
<211> LENGTH: 11
<212> TYPE: PRT
<213> ORGANISM: Homo sapience

<400> SEQUENCE: 49

Ser Pro Thr Tyr Tyr Pro Gly Ala Leu Asp Met
1               5                   10

<210> SEQ ID NO 50
<211> LENGTH: 11
<212> TYPE: PRT
<213> ORGANISM: Homo sapience

<400> SEQUENCE: 50

Ala Pro Leu Ile Tyr Asn Trp Tyr Phe Asp Leu
1               5                   10

<210> SEQ ID NO 51
<211> LENGTH: 11
<212> TYPE: PRT
<213> ORGANISM: Homo sapience

<400> SEQUENCE: 51

Ala Pro Leu Ile Tyr Asn Trp Tyr Tyr Asp Leu
1               5                   10

<210> SEQ ID NO 52
<211> LENGTH: 12
<212> TYPE: PRT
<213> ORGANISM: Homo sapience

<400> SEQUENCE: 52

His Pro Thr Tyr His Tyr Gly Ser Ala Met Asp Tyr
1               5                   10

<210> SEQ ID NO 53
<211> LENGTH: 12

```
<212> TYPE: PRT
<213> ORGANISM: Homo sapience

<400> SEQUENCE: 53

His Pro Thr Tyr Tyr Phe Gly Ser Ala Met Glu Tyr
1               5                   10

<210> SEQ ID NO 54
<211> LENGTH: 12
<212> TYPE: PRT
<213> ORGANISM: Homo sapience

<400> SEQUENCE: 54

His Pro Thr Tyr Tyr Tyr Gly Ser Pro Met Asp Tyr
1               5                   10

<210> SEQ ID NO 55
<211> LENGTH: 12
<212> TYPE: PRT
<213> ORGANISM: Homo sapience

<400> SEQUENCE: 55

His Pro Met Tyr His Tyr Gly Ser Ala Met Asp Tyr
1               5                   10

<210> SEQ ID NO 56
<211> LENGTH: 12
<212> TYPE: PRT
<213> ORGANISM: Homo sapience

<400> SEQUENCE: 56

His Ser Gly Tyr His Leu Ile Gly Tyr Phe Asp Ser
1               5                   10

<210> SEQ ID NO 57
<211> LENGTH: 13
<212> TYPE: PRT
<213> ORGANISM: Homo sapience

<400> SEQUENCE: 57

Glu Glu Gly Tyr Tyr Tyr Gly Ser Gly Pro Leu Asp Ser
1               5                   10

<210> SEQ ID NO 58
<211> LENGTH: 13
<212> TYPE: PRT
<213> ORGANISM: Homo sapience

<400> SEQUENCE: 58

Asn Ser Gly Tyr His Ile Ser Gly Phe Tyr Leu Asp Tyr
1               5                   10

<210> SEQ ID NO 59
<211> LENGTH: 13
<212> TYPE: PRT
<213> ORGANISM: Homo sapience

<400> SEQUENCE: 59

Ser Leu Gly Tyr His Thr Gln Tyr Asn Gly Met Asp Val
1               5                   10

<210> SEQ ID NO 60
<211> LENGTH: 15
<212> TYPE: PRT
<213> ORGANISM: Homo sapience
```

-continued

<400> SEQUENCE: 60

His Pro Thr Tyr His Phe Asp Lys Ser Gly Tyr Arg Phe Asp Ser
1               5                   10                  15

<210> SEQ ID NO 61
<211> LENGTH: 15
<212> TYPE: PRT
<213> ORGANISM: Homo sapience

<400> SEQUENCE: 61

Ser Arg Gly Tyr Ser Phe Gly Tyr Gly Thr Asp Tyr Phe Asp Tyr
1               5                   10                  15

<210> SEQ ID NO 62
<211> LENGTH: 15
<212> TYPE: PRT
<213> ORGANISM: Homo sapience

<400> SEQUENCE: 62

Asn Tyr Tyr Gly Ser Gly Thr Tyr Phe Asn Asp Ala Phe Asp Ile
1               5                   10                  15

<210> SEQ ID NO 63
<211> LENGTH: 14
<212> TYPE: PRT
<213> ORGANISM: Homo sapience

<400> SEQUENCE: 63

Tyr Gln Ser Ser Asp Tyr Tyr Asn Ser Glu Tyr Phe Gln His
1               5                   10

<210> SEQ ID NO 64
<211> LENGTH: 126
<212> TYPE: PRT
<213> ORGANISM: Homo sapience

<400> SEQUENCE: 64

Gln Val Gln Leu Val Gln Ser Gly Ser Glu Val Lys Lys Pro Gly Ala
1               5                   10                  15

Ser Val Lys Val Ser Cys Lys Ala Ser Gly Tyr Thr Phe Thr Ser Asn
                20                  25                  30

Gly Ile Ser Trp Val Arg Gln Ala Pro Gly Gln Gly Leu Glu Trp Met
            35                  40                  45

Gly Trp Ile Ser Gly Leu Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Thr Ser Asp Asp Thr Ala Val Tyr Phe Cys
                85                  90                  95

Ala Arg Asp Thr Thr Val Thr Asn Glu Glu Ile Asn Phe Tyr Tyr Gly
                100                 105                 110

Met Asp Val Trp Gly Gln Gly Thr Thr Val Thr Val Ser Ser
            115                 120                 125

<210> SEQ ID NO 65
<211> LENGTH: 126
<212> TYPE: PRT
<213> ORGANISM: Homo sapience

<400> SEQUENCE: 65

```
Gln Val Gln Leu Val Gln Ser Gly Ala Glu Met Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Asn Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Thr Glu Val Thr Asn Glu Glu Ile Asn Phe Tyr Tyr Gly
                100                 105                 110

Met Asp Val Trp Gly Gln Gly Thr Thr Val Thr Val Ser Ser
                115                 120                 125
```

```
<210> SEQ ID NO 66
<211> LENGTH: 126
<212> TYPE: PRT
<213> ORGANISM: Homo sapience

<400> SEQUENCE: 66

Glu Val Gln Leu Val Glu Ser Gly Ala Glu Met Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Asn Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Thr Glu Val Thr Ser Glu Glu Ile Asn Phe Tyr Tyr Gly
                100                 105                 110

Met Asp Val Trp Gly Gln Gly Thr Leu Val Thr Val Ser Ser
                115                 120                 125
```

```
<210> SEQ ID NO 67
<211> LENGTH: 126
<212> TYPE: PRT
<213> ORGANISM: Homo sapience

<400> SEQUENCE: 67

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Thr Thr Ala Tyr
65                  70                  75                  80
```

```
Met Glu Leu Arg Ser Leu Arg Ser Asp Asp Thr Ala Val Tyr Tyr Cys
            85                  90                  95

Ala Arg Asp Thr Thr Val Thr Ser Glu Glu Ile Asn Phe Tyr Gln Gly
            100                 105                 110

Met Asp Val Trp Gly Gln Gly Thr Thr Val Thr Val Ser Ser
            115                 120                 125

<210> SEQ ID NO 68
<211> LENGTH: 126
<212> TYPE: PRT
<213> ORGANISM: Homo sapience

<400> SEQUENCE: 68

Gln Val Gln Leu Gln Glu Ser Gly Ala Glu Val Lys Lys Pro Gly Ala
1               5                   10                  15

Ser Val Lys Val Ser Cys Lys Ala Ser Gly Tyr Ala Phe Thr Thr Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Tyr Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Glu Phe Gly Ala Asn Gly Glu Asp Ile Tyr Phe Tyr His Gly
            100                 105                 110

Met Asp Val Trp Gly Gln Gly Thr Thr Val Thr Val Ser Ser
            115                 120                 125

<210> SEQ ID NO 69
<211> LENGTH: 129
<212> TYPE: PRT
<213> ORGANISM: Homo sapience

<400> SEQUENCE: 69

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
            35                  40                  45

Trp Leu Ala Leu Ile Tyr Trp Asp Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala His Ser Ile Gly Gly Tyr Asp Gly Glu Gly Ile Phe Tyr Asn
            100                 105                 110

His Tyr Gly Met Asp Val Trp Gly Gln Gly Thr Thr Val Thr Val Ser
            115                 120                 125

Ser

<210> SEQ ID NO 70
<211> LENGTH: 123
<212> TYPE: PRT
```

```
<213> ORGANISM: Homo sapience

<400> SEQUENCE: 70

Glu Val Gln Leu Val Glu Ser Gly Gly Asn Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Thr Trp Val Arg Gln Ala Pro Gly Lys Gly Leu Glu Trp Val
        35                  40                  45

Ala Asn Ile Glu Gln Asp Gly Ser Glu Lys Phe Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Glu Trp Phe Gly Glu Leu Gly Ser Ser Gly Met Asp Val
            100                 105                 110

Trp Gly Gln Gly Thr Thr Val Thr Val Ser Ser
        115                 120
```

```
<210> SEQ ID NO 71
<211> LENGTH: 123
<212> TYPE: PRT
<213> ORGANISM: Homo sapience

<400> SEQUENCE: 71

Gln Val Gln Leu Gln Glu Ser Gly Gly Gly Ser Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp His Ser Gly Ser Ile Gly Tyr Ala Asp Ser Val
    50                  55                  60

Lys Gly Arg Phe Thr Ile Ser Arg Asp Asn Ala Lys Asp Ser Leu Tyr
65                  70                  75                  80

Leu Gln Met Asn Ser Leu Arg Pro Glu Asp Thr Ala Leu Tyr Tyr Cys
                85                  90                  95

Ala Lys Asp Phe Ala Gly Glu Gly His Gly Ser Gly Ser Val Asp Tyr
            100                 105                 110

Trp Gly Gln Gly Thr Leu Val Thr Val Ser Ser
        115                 120
```

```
<210> SEQ ID NO 72
<211> LENGTH: 129
<212> TYPE: PRT
<213> ORGANISM: Homo sapience

<400> SEQUENCE: 72

Glu Val Gln Leu Val Glu Ser Gly Gly Gly Pro Val Lys Pro Gly Gly
1               5                   10                  15

Ser Leu Arg Leu Ser Cys Ala Ala Ser Ala Phe Thr Phe Arg Thr Tyr
            20                  25                  30

Asp Met Asn Trp Val Arg Gln Ala Pro Gly Lys Gly Leu Glu Trp Val
        35                  40                  45

Ser Gly Ile Ser Ser Ser Gly Asp Tyr Ile Tyr Tyr Ala Asp Ser Val
    50                  55                  60
```

```
Gln Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Val Tyr Phe Cys
                85                  90                  95

Ala Lys Ser Ala Thr Ser Tyr Arg Asp Tyr Leu Asp Arg Asp Phe Phe
            100                 105                 110

Tyr Tyr Ala Leu Asp Val Trp Gly Gln Gly Thr Met Val Thr Val Ser
        115                 120                 125

Ser
```

<210> SEQ ID NO 73
<211> LENGTH: 129
<212> TYPE: PRT
<213> ORGANISM: Homo sapience

<400> SEQUENCE: 73

```
Gln Val Gln Leu Gln Glu Ser Gly Gly Gly Leu Val Lys Ser Gly Gly
1               5                   10                  15

Ser Leu Arg Leu Ser Cys Ala Ala Ser Ala Phe Thr Phe Arg Thr Tyr
            20                  25                  30

Asp Met Asn Trp Val Arg Gln Ala Pro Gly Lys Gly Leu Glu Trp Val
        35                  40                  45

Ser Gly Ile Ser Ser Ser Gly Asp Tyr Ile Tyr Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Val Tyr Phe Cys
                85                  90                  95

Ala Lys Ser Ala Thr Ser Tyr Arg Asp Tyr Leu Asp Arg Asp Phe Tyr
            100                 105                 110

Tyr Tyr Ala Leu Asp Val Trp Gly Gln Gly Thr Thr Val Thr Val Ser
        115                 120                 125

Ser
```

<210> SEQ ID NO 74
<211> LENGTH: 126
<212> TYPE: PRT
<213> ORGANISM: Homo sapience

<400> SEQUENCE: 74

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Met Ser Asp Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp His Leu Asn Ser Glu Ile Val Ala Thr Ile Thr Gly Phe
            100                 105                 110

Leu Asp Tyr Trp Gly Gln Gly Thr Leu Val Thr Val Ser Ser
```

```
                115                 120                 125

<210> SEQ ID NO 75
<211> LENGTH: 126
<212> TYPE: PRT
<213> ORGANISM: Homo sapience

<400> SEQUENCE: 75

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ala Val Ile Ser Asp Asp Gly Ile Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Thr Val Tyr Tyr Cys
                85                  90                  95

Ala Arg Asp Lys Leu Asn Ser Glu Met Val Ala Thr Ile Thr Gly Phe
            100                 105                 110

Leu Asp Tyr Trp Gly Gln Gly Thr Leu Val Thr Val Ser Ser
        115                 120                 125

<210> SEQ ID NO 76
<211> LENGTH: 126
<212> TYPE: PRT
<213> ORGANISM: Homo sapience

<400> SEQUENCE: 76

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Ile Ile Ser Asp Asp Gly Thr His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Leu Asn Ser Glu Met Val Ala Thr Ile Thr Gly Phe
            100                 105                 110

Met Asp Tyr Trp Gly Gln Gly Thr Leu Val Thr Val Ser Ser
        115                 120                 125

<210> SEQ ID NO 77
<211> LENGTH: 126
<212> TYPE: PRT
<213> ORGANISM: Homo sapience

<400> SEQUENCE: 77

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

-continued

Gly Met His Trp Val Arg Gln Ala Pro Gly Lys Gly Leu Glu Trp Val
            35                  40                  45

Ala Val Ile Ser Asn Asp Gly Ser Asn Lys Tyr Tyr Ala Asp Ser Val
        50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Val Tyr His Cys
                85                  90                  95

Gly Arg Asp Lys Leu Asn Ser Asp Glu Val Thr Thr Ile Thr Gly Phe
            100                 105                 110

Leu Asp Tyr Trp Gly Gln Gly Thr Leu Val Thr Val Ser Ser
        115                 120                 125

<210> SEQ ID NO 78
<211> LENGTH: 126
<212> TYPE: PRT
<213> ORGANISM: Homo sapience

<400> SEQUENCE: 78

Glu Val Gln Leu Val Glu Ser Gly Gly Val Val Gln Pro Gly Arg
1               5                   10                  15

Ser Leu Arg Leu Ser Cys Ala Val Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Val Ser Asp Asp Glu Ser Tyr Lys Tyr Tyr Ala Asp Ser Val
    50                  55                  60

Lys Gly Arg Phe Ile Ile Ser Arg Asp Asn Ser Lys Asn Thr Leu Tyr
65                  70                  75                  80

Leu Gln Ile Asn Ser Leu Arg Ala Glu Asp Thr Ala Val Tyr Ser Cys
                85                  90                  95

Ala Arg Asp Asn Leu Asn Ser Glu Leu Val Ala Thr Ile Thr Gly Phe
            100                 105                 110

Leu Asp His Trp Gly Gln Gly Thr Leu Val Thr Val Ser Ser
        115                 120                 125

<210> SEQ ID NO 79
<211> LENGTH: 126
<212> TYPE: PRT
<213> ORGANISM: Homo sapience

<400> SEQUENCE: 79

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Arg Asp Asn Leu Asn Ser Asp Glu Val Ala Thr Ile Ser Gly Phe
            100                 105                 110

-continued

```
Leu Asp Tyr Trp Gly Gln Gly Thr Leu Val Thr Val Ser Ser
            115                 120                 125

<210> SEQ ID NO 80
<211> LENGTH: 126
<212> TYPE: PRT
<213> ORGANISM: Homo sapience

<400> SEQUENCE: 80

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Ala Met His Trp Val Arg Gln Ala Pro Gly Lys Gly Leu Glu Trp Val
            35                  40                  45

Ala Leu Ile Ser Ser Asp Gly Ser Tyr Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Leu Asn Ser Glu Met Val Ala Thr Ile Thr Gly Phe
            100                 105                 110

Leu Asp Ser Trp Gly Gln Gly Thr Leu Val Thr Val Ser Ser
            115                 120                 125

<210> SEQ ID NO 81
<211> LENGTH: 126
<212> TYPE: PRT
<213> ORGANISM: Homo sapience

<400> SEQUENCE: 81

Glu Val Gln Leu Val Glu Ser Gly Gly Val Val Gln Pro Gly Arg
1               5                   10                  15

Ser Leu Arg Leu Ser Cys Ala Ala Ser Gly Phe Ser Phe Ser Ser Tyr
            20                  25                  30

Ala Val His Trp Val Arg Gln Ala Pro Gly Lys Gly Leu Glu Trp Val
            35                  40                  45

Ala Asp Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Thr Glu Pro Ser Asn Thr Glu Asp Ile Arg Gly Ile Glu Gly Val
            100                 105                 110

Phe Asp Tyr Trp Gly Gln Gly Thr Leu Val Thr Val Ser Ser
            115                 120                 125

<210> SEQ ID NO 82
<211> LENGTH: 124
<212> TYPE: PRT
<213> ORGANISM: Homo sapience

<400> SEQUENCE: 82

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Ser Phe Ser Gln Tyr
            20                  25                  30

Gly Met His Trp Val Arg Gln Ala Pro Gly Lys Gly Leu Glu Trp Val
            35                  40                  45

Ala Leu Ile Tyr Tyr Gly Gly Asn Pro Lys Ser Tyr Ala Asp Ser Val
    50                  55                  60

Lys Gly Arg Phe Thr Ile Ser Arg Asp Asn Ser Arg Asn Thr Leu Ser
65                  70                  75                  80

Leu Glu Met Asn Asn Leu Arg Thr Glu Asp Thr Ala Ile Tyr Tyr Cys
                85                  90                  95

Ala Arg Asp Ala Tyr Ser Ser Gly Asp Thr Tyr Tyr Tyr Gly Leu Asp
            100                 105                 110

Val Trp Gly Gln Gly Thr Met Val Thr Val Ser Ser
            115                 120
```

<210> SEQ ID NO 83
<211> LENGTH: 126
<212> TYPE: PRT
<213> ORGANISM: Homo sapience

<400> SEQUENCE: 83

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Arg Ala Pro Gly Lys Gly Leu Glu Trp Val
            35                  40                  45

Ser Val Ile Asp Gly Asp Gly Gly Ser Thr Tyr Tyr Ala Asp Ser Val
    50                  55                  60

Lys Gly Arg Phe Thr Ile Ser Arg Asp Asn Ser Lys Lys Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Arg Gly Thr Gly Glu Gln Ile Ala Val Val Thr Ala Leu
            100                 105                 110

Ile Asp Tyr Trp Gly Gln Gly Thr Leu Val Thr Val Ser Ser
            115                 120                 125
```

<210> SEQ ID NO 84
<211> LENGTH: 122
<212> TYPE: PRT
<213> ORGANISM: Homo sapience

<400> SEQUENCE: 84

```
Glu Val Gln Leu Val Glu Ser Gly Pro Gly Leu Val Lys Pro Ser Glu
1               5                   10                  15

Thr Leu Ser Leu Thr Cys Thr Val Ser Gly Gly Ser Ile Ser Ser Asp
            20                  25                  30

Ser Tyr Tyr Trp Asp Trp Ile Arg Gln Pro Pro Gly Lys Gly Leu Glu
            35                  40                  45

Trp Ile Gly Asn Ile Tyr Tyr Ser Gly Ser Thr Tyr Tyr Asn Ser Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

```
Cys Ala Arg His Gly Tyr Gly Asp Tyr Val Gly Tyr Phe Asp Tyr Trp
            100                 105                 110

Gly Gln Gly Thr Leu Val Thr Val Ser Ser
        115                 120
```

<210> SEQ ID NO 85
<211> LENGTH: 123
<212> TYPE: PRT
<213> ORGANISM: Homo sapience

<400> SEQUENCE: 85

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser His
            20                  25                  30

Tyr Trp Ser Trp Ile Arg Gln Pro Gly Lys Gly Leu Glu Trp Ile
        35                  40                  45

Gly Tyr Ile Tyr Tyr Gly Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Leu Arg Trp Leu Gly Glu Glu Asp Ala Asp Ala Phe Asp Ile
            100                 105                 110

Trp Gly Gln Gly Thr Thr Val Thr Val Ser Ser
        115                 120
```

<210> SEQ ID NO 86
<211> LENGTH: 126
<212> TYPE: PRT
<213> ORGANISM: Homo sapience

<400> SEQUENCE: 86

```
Glu Val Gln Leu Val Glu Ser Gly Pro Gly Leu Val Lys Pro Ser Glu
1               5                   10                  15

Thr Leu Ser Leu Thr Cys Thr Val Ser Gly Gly Ser Met Thr Thr His
            20                  25                  30

Tyr Trp Asn Trp Ile Arg Gln Pro Pro Gly Lys Ala Leu Glu Trp Ile
        35                  40                  45

Gly Asn Ile Tyr Tyr Ser Gly Gly Thr Glu Tyr Asn Pro Ser Leu Gln
    50                  55                  60

Ser Arg Leu Thr Ile Ser Leu Asp Thr Ser Lys Asn Gln Phe Ser Leu
65                  70                  75                  80

Thr Leu Thr Ser Gly Thr Ala Ala Asp Thr Ala Val Tyr Tyr Cys Ala
                85                  90                  95

Arg Gly Phe Gly Met Val Gly Asp Thr Val Asp Asp Leu Tyr Asn Gly
            100                 105                 110

Met Asp Val Trp Gly Gln Gly Thr Thr Val Thr Val Ser Ser
        115                 120                 125
```

<210> SEQ ID NO 87
<211> LENGTH: 123
<212> TYPE: PRT
<213> ORGANISM: Homo sapience

<400> SEQUENCE: 87

```
Glu Val Gln Leu Val Glu Ser Val Pro Gly Leu Val Lys Pro Ser Glu
```

```
1               5                   10                  15
Thr Leu Ser Leu Thr Cys Thr Val Gly Gly Ser Ile Ser Thr Tyr
                20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Arg Ser Val Thr Ala Ala Asp Thr Ala Val Tyr Tyr Cys Ala
                85                  90                  95

Arg Val Gln Arg Pro Tyr Gly Asp Tyr Ala Ala Gly Ala Phe Asp Ile
                100                 105                 110

Trp Gly Gln Gly Thr Thr Val Thr Val Ser Ser
            115                 120
```

<210> SEQ ID NO 88
<211> LENGTH: 123
<212> TYPE: PRT
<213> ORGANISM: Homo sapience

<400> SEQUENCE: 88

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Thr Tyr
                20                  25                  30

Tyr Trp Ser Trp Ile Arg Gln Pro Pro Gly Lys Gly Leu Glu Trp Val
        35                  40                  45

Gly Tyr Ile Asp Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Ile Leu Arg Ser Val Thr Ala Ala Asp Thr Ala Val Tyr Tyr Cys Ala
                85                  90                  95

Arg Val Gln Arg Pro Tyr Gly Asp Tyr Ile Thr Gly Ala Phe Asp Ile
                100                 105                 110

Trp Gly Gln Gly Thr Thr Val Thr Val Ser Ser
            115                 120
```

<210> SEQ ID NO 89
<211> LENGTH: 128
<212> TYPE: PRT
<213> ORGANISM: Homo sapience

<400> SEQUENCE: 89

```
Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
                20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Gly Met Tyr Tyr Cys
```

```
                     85                  90                  95

Ala Arg Arg Thr Trp Tyr Tyr Asp Gly Ser Gly Pro Asp Pro Ser Arg
                100                 105                 110

Asp Ala Phe Asp Ile Trp Gly Gln Gly Thr Met Val Thr Val Ser Ser
            115                 120                 125
```

<210> SEQ ID NO 90
<211> LENGTH: 128
<212> TYPE: PRT
<213> ORGANISM: Homo sapience

<400> SEQUENCE: 90

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Leu Gly Asn Gly Glu Asp Ile Ala Val Gln Pro Gly Thr
                100                 105                 110

Ile Gly Val Asp Tyr Trp Gly Gln Gly Thr Leu Val Thr Val Ser Ser
            115                 120                 125
```

<210> SEQ ID NO 91
<211> LENGTH: 128
<212> TYPE: PRT
<213> ORGANISM: Homo sapience

<400> SEQUENCE: 91

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
        50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Leu Gly Asn Gly Glu Asp Ile Ala Val Gln Pro Gly Thr
                100                 105                 110

Thr Gly Val Asp Tyr Trp Gly Gln Gly Thr Leu Val Thr Val Ser Ser
            115                 120                 125
```

<210> SEQ ID NO 92
<211> LENGTH: 128
<212> TYPE: PRT
<213> ORGANISM: Homo sapience

<400> SEQUENCE: 92

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Ser Ser Tyr
            20                  25                  30

Ala Met Asn Trp Val Arg Gln Ala Pro Gly Gln Gly Leu Glu Trp Met
        35                  40                  45

Gly Trp Val Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Leu Gly Asn Gly Glu Asp Ile Val Val Gln Pro Ala Thr
            100                 105                 110

Ile Gly Val Asp Tyr Trp Gly Gln Gly Thr Leu Val Thr Val Ser Ser
        115                 120                 125

<210> SEQ ID NO 93
<211> LENGTH: 126
<212> TYPE: PRT
<213> ORGANISM: Homo sapience

<400> SEQUENCE: 93

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Ser Ser Tyr
            20                  25                  30

Gly Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Ser Gly Thr Glu Val Thr Thr Glu Glu Ile Tyr Phe Tyr Tyr Gly
            100                 105                 110

Met Asp Val Trp Gly Gln Gly Thr Met Val Thr Val Ser Ser
        115                 120                 125

<210> SEQ ID NO 94
<211> LENGTH: 126
<212> TYPE: PRT
<213> ORGANISM: Homo sapience

<400> SEQUENCE: 94

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Ile Ser Tyr
            20                  25                  30

Thr Met Asn Trp Val Arg Gln Ala Pro Gly Gln Gly Leu Glu Trp Met
        35                  40                  45

Gly Trp Ile Asn Thr Asn Thr Gly Asn Pro Arg Tyr Ala Gln Gly Phe
    50                  55                  60

Thr Gly Arg Phe Val Phe Ser Leu Asp Thr Ser Val Ser Thr Ala Tyr
65                  70                  75                  80
```

```
Leu Gln Ile Ser Ser Leu Lys Ala Glu Asp Thr Ala Val Tyr Tyr Cys
                85                  90                  95

Ala Arg Gly Thr Glu Val Thr Thr Glu Glu Ile Asn Phe Tyr Tyr Gly
            100                 105                 110

Met Asp Val Trp Gly Gln Gly Thr Thr Val Thr Val Ser Ser
        115                 120                 125

<210> SEQ ID NO 95
<211> LENGTH: 125
<212> TYPE: PRT
<213> ORGANISM: Homo sapience

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Asn Ser Tyr
                20                  25                  30

Ala Ile His Trp Val Arg Gln Ala Pro Gly Gln Arg Pro Glu Trp Met
            35                  40                  45

Gly Trp Ile Asn Ile Gly Asn Gly Asn Thr Lys Tyr Ser Gln Lys Phe
        50                  55                  60

Gln Gly Arg Val Ala Ile Thr Arg Asp Arg Ser Ala Ser Thr Ala Tyr
65                  70                  75                  80

Met Glu Val Thr Ser Leu Arg Phe Glu Asp Thr Ala Val Tyr Tyr Cys
                85                  90                  95

Ala Thr Ala Glu Lys Trp Leu Ala Asp Tyr Phe Tyr Tyr Phe Gly Met
            100                 105                 110

Asp Val Trp Gly Arg Gly Thr Thr Val Thr Val Ser Ser
        115                 120                 125

<210> SEQ ID NO 96
<211> LENGTH: 129
<212> TYPE: PRT
<213> ORGANISM: Homo sapience

<400> SEQUENCE: 96

Glu Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Ser Ala Tyr
                20                  25                  30

Tyr Ile His Trp Val Arg Gln Ser Pro Gly Gln Gly Leu Glu Trp Met
            35                  40                  45

Gly Val Ile Asn Pro Ser Gly Gly Asp Thr Asn Tyr Ala Gln Arg Phe
        50                  55                  60

Gln Gly Arg Leu Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Glu Glu Ser Leu Phe Ala Gly Ala Ile Tyr Asn Tyr
            100                 105                 110

Tyr Tyr Asp Met Asp Val Trp Gly Gln Gly Thr Thr Val Thr Val Ser
        115                 120                 125

Ser

<210> SEQ ID NO 97
<211> LENGTH: 126
```

```
<212> TYPE: PRT
<213> ORGANISM: Homo sapience

<400> SEQUENCE: 97

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Lys Asn Asn Pro Ser Leu Lys
    50                  55                  60

Ser Arg Val Thr Ile Ser Val Asp Thr Ser Lys Asn Gln Phe Ser Leu
65              70                  75                  80

Lys Leu Ser Ser Val Thr Ala Ala Asp Thr Ala Val Tyr Tyr Cys Ala
            85                  90                  95

Arg Lys Gly Gly Ala Lys Leu Leu Tyr Phe Asp Trp Leu Ala Ser Ala
        100                 105                 110

Phe Asp Ile Trp Gly Gln Gly Thr Thr Val Thr Val Ser Ser
    115                 120                 125

<210> SEQ ID NO 98
<211> LENGTH: 120
<212> TYPE: PRT
<213> ORGANISM: Homo sapience

<400> SEQUENCE: 98

Gln Val Gln Leu Gln Glu Ser Gly Ala Glu Val Lys Lys Pro Gly Ser
1               5                   10                  15

Ser Val Lys Val Ser Cys Lys Ala Ser Gly Gly Ile Phe Arg Arg Asn
            20                  25                  30

Ala Ile Ser Trp Val Arg Gln Ala Pro Gly Gln Gly Leu Glu Trp Met
        35                  40                  45

Gly Gly Ile Ile Ala Ile Phe Gly Thr Ala Asn Tyr Ala Gln Lys Phe
    50                  55                  60

Gln Gly Arg Val Thr Ile Thr Ala Asp Glu Ser Thr Ser Thr Val Tyr
65              70                  75                  80

Met Glu Leu Ser Ser Leu Arg Pro Glu Asp Thr Ala Val Tyr Tyr Cys
            85                  90                  95

Ala Arg Gly Pro Asn Tyr Tyr Glu Asn Phe Phe Asp Tyr Trp Gly Gln
        100                 105                 110

Gly Thr Leu Val Thr Val Ser Ser
    115                 120

<210> SEQ ID NO 99
<211> LENGTH: 120
<212> TYPE: PRT
<213> ORGANISM: Homo sapience

<400> SEQUENCE: 99

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Ser Asn
            20                  25                  30

Ala Val Ser Trp Val Arg Gln Ala Pro Gly Gln Gly Leu Glu Trp Met
        35                  40                  45

Gly Gly Ile Ile Ala Ile Phe Gly Thr Pro Lys Tyr Ala Gln Lys Phe
```

```
            50                  55                  60
Gln Gly Arg Val Thr Ile Thr Ala Asp Glu Ser Thr Ser Thr Val Tyr
 65                  70                  75                  80

Met Glu Leu Ser Gly Leu Arg Tyr Glu Asp Thr Ala Val Tyr Tyr Cys
                 85                  90                  95

Ala Arg Gly Pro Asn Tyr Tyr Glu Ser Tyr Phe Asp Tyr Trp Gly Gln
                100                 105                 110

Gly Thr Leu Val Thr Val Ser Ser
            115                 120

<210> SEQ ID NO 100
<211> LENGTH: 120
<212> TYPE: PRT
<213> ORGANISM: Homo sapience

<400> SEQUENCE: 100

Gln Val Gln Leu Gln Gln Ser Gly Ala Glu Val Lys Lys Pro Gly Ser
 1               5                  10                  15

Ser Val Lys Val Ser Cys Lys Ala Ser Gly Gly Ile Phe Arg Lys Asn
                 20                  25                  30

Ala Ile Ser Trp Val Arg Gln Ala Pro Gly Gln Gly Leu Glu Trp Met
             35                  40                  45

Gly Gly Ile Ile Ala Ile Phe Gly Thr Ala Asn Tyr Ala Gln Lys Phe
     50                  55                  60

Gln Gly Arg Val Thr Ile Thr Ala Asp Asp Ser Thr Asn Thr Val Tyr
 65                  70                  75                  80

Met Glu Leu Thr Ser Leu Arg Tyr Glu Asp Thr Ala Val Tyr Tyr Cys
                 85                  90                  95

Ala Arg Gly Pro Asn Tyr Tyr Glu Asn Tyr Phe Asp Phe Trp Gly Gln
                100                 105                 110

Gly Thr Leu Val Thr Val Ser Ser
            115                 120

<210> SEQ ID NO 101
<211> LENGTH: 120
<212> TYPE: PRT
<213> ORGANISM: Homo sapience

<400> SEQUENCE: 101

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Ile Phe Arg Lys Ser
                 20                  25                  30

Ala Ile Thr Trp Val Arg Gln Ala Pro Gly Gln Gly Leu Glu Trp Met
             35                  40                  45

Gly Gly Ile Ile Ala Ile Phe Gly Thr Thr Asn Tyr Ala Gln Lys Phe
     50                  55                  60

Gln Asp Arg Val Thr Ile Thr Ala Asp Asp Ser Thr Asn Thr Val Tyr
 65                  70                  75                  80

Met Glu Leu Thr Ser Leu Arg Tyr Glu Asp Thr Ala Val Tyr Tyr Cys
                 85                  90                  95

Ala Arg Gly Pro Asn Tyr Tyr Glu Ser Tyr Leu Asp Phe Trp Gly Gln
                100                 105                 110

Gly Thr Thr Val Thr Val Ser Ser
            115                 120
```

-continued

<210> SEQ ID NO 102
<211> LENGTH: 120
<212> TYPE: PRT
<213> ORGANISM: Homo sapience

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Ser His
                20                  25                  30

Ala Ile Ser Trp Val Arg Gln Ala Pro Gly Gln Gly Leu Glu Trp Met
            35                  40                  45

Gly Gly Ile Ile Ala Ile Phe Gly Thr Thr His Tyr Ala Gln Gln Phe
    50                  55                  60

Gln Gly Arg Val Thr Ile Thr Ala Asp Glu Ser Thr Ser Thr Val Tyr
65                  70                  75                  80

Met Glu Leu Ser Thr Leu Arg Ser Glu Asp Thr Ala Val Tyr Tyr Cys
                85                  90                  95

Ala Arg Gly Pro Asn Tyr Phe Glu Ser Tyr Phe Asp Asn Trp Gly Gln
                100                 105                 110

Gly Thr Leu Val Thr Val Ser Ser
            115                 120

<210> SEQ ID NO 103
<211> LENGTH: 120
<212> TYPE: PRT
<213> ORGANISM: Homo sapience

<400> SEQUENCE: 103

Gln Val Gln Leu Val Gln Ser Gly Ala Glu Val Lys Lys Pro Gly Ser
1               5                   10                  15

Ser Val Lys Val Ser Cys Lys Ala Ser Gly Asp Ile Phe Asn Lys Phe
                20                  25                  30

Ala Ile Thr Trp Val Arg Gln Ala Pro Gly Gln Gly Leu Glu Trp Met
            35                  40                  45

Gly Gly Ile Thr Ala Leu Phe Ala Thr Thr Ser Tyr Ala Gln Lys Phe
    50                  55                  60

Gln Asp Arg Val Thr Ile Asn Trp Asp Glu Ser Thr Thr Thr Ala Phe
65                  70                  75                  80

Met Glu Leu Ser Ser Leu Arg Phe Glu Asp Thr Ala Val Tyr Tyr Cys
                85                  90                  95

Ala Arg Gly Pro Asn Tyr Tyr Glu Thr Tyr Leu Asp Asn Trp Gly Gln
                100                 105                 110

Gly Thr Leu Val Thr Val Ser Ser
            115                 120

<210> SEQ ID NO 104
<211> LENGTH: 122
<212> TYPE: PRT
<213> ORGANISM: Homo sapience

<400> SEQUENCE: 104

Gln Val Gln Leu Val Gln Ser Gly Ser Glu Val Lys Lys Pro Gly Ser
1               5                   10                  15

Ser Val Lys Val Ser Cys Ser Phe Lys Ala Ser Gly Gly Ile Ile Ser
                20                  25                  30

Lys Tyr Ala Ile Thr Trp Val Arg Gln Ala Pro Gly Gln Gly Leu Glu
            35                  40                  45

Trp Met Gly Gly Ile Ala Ile Phe Gly Ser Thr Asn Tyr Ala Gln
            50                  55                  60

Lys Phe Gln Gly Arg Leu Thr Ile Thr Ser Asp Glu Ser Thr Ser Thr
65                  70                  75                  80

Ala Tyr Met Glu Leu Ser Ser Leu Thr Ser Glu Asp Thr Ala Val Tyr
                85                  90                  95

Tyr Cys Gly Arg Gly Pro His Tyr Tyr Glu Ser His Leu Asp Tyr Trp
                100                 105                 110

Gly Gln Gly Thr Leu Val Thr Val Ser Ser
            115                 120

<210> SEQ ID NO 105
<211> LENGTH: 120
<212> TYPE: PRT
<213> ORGANISM: Homo sapience

<400> SEQUENCE: 105

Gln Val Gln Leu Val Gln Ser Gly Ser Glu Val Lys Lys Pro Gly Ser
1               5                   10                  15

Ser Val Lys Val Ser Cys Lys Ser Ser Gly Gly Ile Leu Arg Arg Ser
            20                  25                  30

Ala Ile Ser Trp Val Arg Gln Ala Pro Gly Gln Gly Leu Glu Trp Met
        35                  40                  45

Gly Gly Ile Leu Ala Ile Phe Gly Thr Thr Lys Tyr Ala Gln Lys Phe
    50                  55                  60

Gln Gly Arg Ile Thr Ile Thr Ala Asp Glu Ser Thr Asn Thr Val His
65                  70                  75                  80

Met Glu Leu Ser Ser Leu Arg Pro Asp Asp Thr Ala Val Tyr Tyr Cys
                85                  90                  95

Ala Gly Gly Pro His Tyr Tyr Val Ser Tyr Phe Asp Ser Trp Gly Gln
                100                 105                 110

Gly Thr Leu Val Thr Val Ser Ser
            115                 120

<210> SEQ ID NO 106
<211> LENGTH: 120
<212> TYPE: PRT
<213> ORGANISM: Homo sapience

<400> SEQUENCE: 106

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Asn Lys Tyr
            20                  25                  30

Gly Ile Ser Trp Val Arg Gln Ala Pro Gly Gln Gly Leu Glu Trp Met
        35                  40                  45

Gly Gly Ile Leu Ala Ile Phe Gly Thr Thr Asn Tyr Ala Gln Lys Phe
    50                  55                  60

Gln Gly Arg Val Thr Ile Ser Ala Asp Glu Ser Ser Thr Thr Val Tyr
65                  70                  75                  80

Met Glu Leu Ser Ser Leu Thr Ser Glu Asp Thr Ala Val Tyr Tyr Cys
                85                  90                  95

Ala Arg Gly Asn Thr Tyr Tyr Ser Ser Tyr Phe Asp Gln Trp Gly Gln
                100                 105                 110

Gly Thr Leu Val Thr Val Ser Ser
            115                 120

<210> SEQ ID NO 107
<211> LENGTH: 120
<212> TYPE: PRT
<213> ORGANISM: Homo sapience

<400> SEQUENCE: 107

Gln Val Gln Leu Val Gln Ser Gly Ser Glu Val Lys Lys Pro Gly Ser
1               5                   10                  15

Ser Val Lys Val Ser Cys Lys Ala Ser Gly Gly Ile Phe Asn Ser Tyr
            20                  25                  30

Gly Ile Ser Trp Val Arg Gln Ala Pro Gly Gln Gly Leu Glu Trp Met
        35                  40                  45

Gly Gly Ile Leu Ala Ile Phe Gly Thr Thr Asn Tyr Ala Gln Lys Phe
    50                  55                  60

Gln Gly Arg Val Thr Ile Thr Ala Asp Asp Ser Lys Thr Val Tyr
65                  70                  75                  80

Met Glu Leu Ser Ser Leu Thr Ser Glu Asp Thr Ala Val Tyr Tyr Cys
                85                  90                  95

Ala Arg Gly Ser Thr Tyr Tyr Ser Tyr Phe Asp Gln Trp Gly Gln
            100                 105                 110

Gly Thr Leu Val Thr Val Ser Ser
        115                 120

<210> SEQ ID NO 108
<211> LENGTH: 120
<212> TYPE: PRT
<213> ORGANISM: Homo sapience

<400> SEQUENCE: 108

Gln Val Gln Leu Val Gln Ser Gly Ser Glu Val Lys Lys Pro Gly Ser
1               5                   10                  15

Ser Val Lys Val Ser Cys Lys Ala Ser Gly Gly Ile Phe Arg Thr Asn
            20                  25                  30

Ala Ile Ser Tyr Val Arg Gln Ala Pro Gly Gln Gly Leu Glu Trp Met
        35                  40                  45

Gly Gly Ile Thr Ala Ile Phe Gly Thr Pro Asn Tyr Ala Gln Lys Phe
    50                  55                  60

Gln Gly Arg Val Thr Ile Ile Ala Asp Glu Ser Thr Ser Thr Val Tyr
65                  70                  75                  80

Met Glu Leu Gly Ser Leu Thr Ser Glu Asp Thr Ala Val Tyr Tyr Cys
                85                  90                  95

Ala Thr Ser Gly Thr Tyr Tyr Val Ser Tyr Phe Asp Ser Trp Gly Gln
            100                 105                 110

Gly Thr Leu Val Thr Val Ser Ser
        115                 120

<210> SEQ ID NO 109
<211> LENGTH: 120
<212> TYPE: PRT
<213> ORGANISM: Homo sapience

<400> SEQUENCE: 109

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Arg Lys Asn
            20                  25                  30

```
Ala Ile Ser Tyr Val Arg Gln Ala Pro Gly Gln Gly Val Glu Trp Met
            35                  40                  45

Gly Gly Ile Thr Ala Ile Phe Gly Thr Pro Asn Tyr Ala Gln Lys Phe
 50                      55                  60

Gln Gly Arg Ile Thr Ile Ser Ala Asp Glu Ser Thr Asn Thr Val Tyr
65                  70                  75                  80

Met Glu Leu Gly Ser Leu Thr Ser Glu Asp Thr Ala Val Tyr Tyr Cys
                85                  90                  95

Ala Thr Ser Gly Thr Tyr Tyr Val Ser Tyr Leu Asp Ser Trp Gly Gln
                100                 105                 110

Gly Thr Leu Val Thr Val Ser Ser
            115                 120

<210> SEQ ID NO 110
<211> LENGTH: 120
<212> TYPE: PRT
<213> ORGANISM: Homo sapience

<400> SEQUENCE: 110

Gln Val Gln Leu Val Gln Ser Gly Ala Glu Val Lys Lys Pro Gly Ser
1               5                   10                  15

Ser Val Lys Leu Ser Cys Lys Ala Ser Gly Gly Thr Leu Arg Ser Tyr
            20                  25                  30

Ala Leu Ser Trp Val Arg Gln Ala Pro Gly Glu Gly Leu Glu Trp Met
            35                  40                  45

Gly Gly Ile Ser Ala Ile Phe Asn Thr Ala Thr Tyr Ala Gln Asn Val
 50                      55                  60

Gln Gly Arg Val Thr Ile Thr Ala Asp Glu Ser Thr Asn Thr Phe Tyr
65                  70                  75                  80

Leu Glu Val Ser Ser Leu Arg Ser Asp Asp Thr Ala Val Tyr Tyr Cys
                85                  90                  95

Ala Thr Ser Gly Thr Tyr Tyr Val Ser Phe Phe Asp Tyr Trp Gly Gln
                100                 105                 110

Gly Thr Leu Val Thr Val Ser Ser
            115                 120

<210> SEQ ID NO 111
<211> LENGTH: 120
<212> TYPE: PRT
<213> ORGANISM: Homo sapience

<400> SEQUENCE: 111

Glu Val Gln Leu Val Glu Ser Gly Ala Glu Val Lys Lys Pro Gly Ser
1               5                   10                  15

Ser Val Lys Val Ser Cys Lys Ala Ser Gly Gly His Phe Asn Ala Tyr
            20                  25                  30

Gly Ile Ser Trp Val Arg Gln Ala Pro Gly Gln Gly Leu Glu Trp Met
            35                  40                  45

Gly Gly Ile Val Ala Leu Phe Gly Thr Thr Asn Tyr Ala Gln Lys Leu
 50                      55                  60

Gln Gly Arg Val Thr Ile Thr Ala Asp Ala Ser Thr Asn Thr Val Tyr
65                  70                  75                  80

Met Glu Leu Thr Ser Leu Arg Ser Asp Asp Thr Ala Val Tyr Tyr Cys
                85                  90                  95

Ala Arg Ser Gly Ser Tyr Tyr Pro Asp Tyr Phe Gln Tyr Trp Gly Gln
                100                 105                 110
```

```
Gly Thr Leu Val Thr Val Ser Ser
        115                 120

<210> SEQ ID NO 112
<211> LENGTH: 120
<212> TYPE: PRT
<213> ORGANISM: Homo sapience

<400> SEQUENCE: 112

Gln Val Gln Leu Val Gln Ser Gly Ser Glu Val Lys Lys Pro Gly Ser
1               5                   10                  15

Ser Val Lys Val Ser Cys Lys Ala Ser Gly Val Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ser Pro Met Phe Gly Thr Thr Arg Tyr Ala Gln Lys Phe
    50                  55                  60

Gln Gly Arg Val Thr Ile Thr Ala Asp Glu Ser Thr Arg Thr Gly Phe
65                  70                  75                  80

Met Glu Leu Ser Ser Leu Arg Ser Gly Asp Thr Ala Val Tyr Tyr Cys
                85                  90                  95

Ala Arg Ser Pro Thr Tyr Tyr Pro Gly Ala Leu Asp Met Trp Gly Gln
            100                 105                 110

Gly Thr Thr Val Thr Val Ser Ser
        115                 120

<210> SEQ ID NO 113
<211> LENGTH: 120
<212> TYPE: PRT
<213> ORGANISM: Homo sapience

<400> SEQUENCE: 113

Glu Val Gln Leu Val Glu Ser Gly Ala Glu Val Lys Lys Pro Gly Ser
1               5                   10                  15

Ser Val Lys Val Ser Cys Lys Ala Ser Gly Ser Ile Phe Ser Asn Tyr
            20                  25                  30

Ala Ile Ser Trp Val Arg Gln Ala Pro Gly Gln Gly Leu Glu Trp Met
        35                  40                  45

Gly Gly Ile Val Pro Met Phe Gly Thr Thr Arg Phe Ala Gln Lys Phe
    50                  55                  60

Gln Gly Arg Val Thr Ile Thr Ala Asp Glu Ser Arg Ser Thr Ala Tyr
65                  70                  75                  80

Met Glu Leu Asn Asn Leu Ile Ser Glu Asp Thr Ala Val Tyr Tyr Cys
                85                  90                  95

Ala Arg Ala Pro Leu Ile Tyr Asn Trp Tyr Phe Asp Leu Trp Gly Arg
            100                 105                 110

Gly Thr Leu Val Thr Val Ser Ser
        115                 120

<210> SEQ ID NO 114
<211> LENGTH: 120
<212> TYPE: PRT
<213> ORGANISM: Homo sapience

<400> SEQUENCE: 114

Glu Val Gln Leu Val Gln Ser Gly Ala Glu Val Lys Lys Pro Gly Ser
1               5                   10                  15

Ser Val Lys Val Ser Cys Gln Ala Ser Gly Ser Ile Phe Ser Asn Tyr
```

```
            20                  25                  30
Ala Ile Asn Trp Val Arg Gln Ala Pro Gly Gln Gly Leu Glu Trp Met
            35                  40                  45

Gly Gly Ile Val Pro Ile Phe Gly Thr Thr Arg Phe Ala Gln Lys Phe
        50                  55                  60

Gln Gly Arg Leu Thr Ile Thr Ala Asp Glu Pro Arg Ser Thr Ala Tyr
65                  70                  75                  80

Met Glu Leu Asn Asn Leu Ile Ser Glu Asp Thr Ala Val Tyr Tyr Cys
                85                  90                  95

Ala Arg Ala Pro Leu Ile Tyr Asn Trp Tyr Tyr Asp Leu Trp Gly Arg
            100                 105                 110

Gly Thr Leu Val Thr Val Ser Ser
            115                 120

<210> SEQ ID NO 115
<211> LENGTH: 121
<212> TYPE: PRT
<213> ORGANISM: Homo sapience

<400> SEQUENCE: 115

Gln Val Gln Leu Gln Gln Ser Gly Ala Asp Val Lys Lys Ala Gly Ser
1               5                   10                  15

Ser Val Lys Val Ser Cys Lys Ala Ser Gly Arg Thr Phe Gly Asn Tyr
            20                  25                  30

Ala Ile Ser Trp Val Arg Gln Ala Pro Gly Gln Gly Leu Glu Trp Met
            35                  40                  45

Gly Gly Ile Thr Pro Ile Phe Gly Ala Ala Asn Tyr Ala Gln Lys Phe
        50                  55                  60

Gln Gly Arg Val Thr Ile Ser Ala Asp Leu Ser Thr Arg Met Val Tyr
65                  70                  75                  80

Met Asp Leu Ser Ser Leu Arg Ser Asp Asp Thr Ala Phe Tyr Tyr Cys
                85                  90                  95

Ala Gly His Pro Thr Tyr His Tyr Gly Ser Ala Met Asp Tyr Trp Gly
            100                 105                 110

Gln Gly Thr Leu Val Thr Val Ser Ser
            115                 120

<210> SEQ ID NO 116
<211> LENGTH: 121
<212> TYPE: PRT
<213> ORGANISM: Homo sapience

<400> SEQUENCE: 116

Gln Val Gln Leu Gln Gln Ser Gly Ala Asp Val Lys Lys Pro Gly Ser
1               5                   10                  15

Ser Val Lys Val Ser Cys Lys Ala Ser Gly Gly Thr Phe Gly Asn Tyr
            20                  25                  30

Ala Ile Ser Trp Val Arg Gln Ala Pro Gly Gln Gly Leu Glu Trp Met
            35                  40                  45

Gly Gly Ile Thr Pro Ile Phe Gly Pro Ala Asn Tyr Ala Gln Arg Phe
        50                  55                  60

Gln Gly Arg Val Thr Ile Ser Ala Asp Ile Ser Thr Arg Thr Ala Tyr
65                  70                  75                  80

Met Glu Leu Ser Ser Leu Arg Ser Glu Asp Thr Ala Ile Tyr Tyr Cys
                85                  90                  95

Ala Arg His Pro Thr Tyr Tyr Phe Gly Ser Ala Met Glu Tyr Trp Gly
```

Gln Gly Thr Leu Val Thr Val Ser Ser
        115                 120

<210> SEQ ID NO 117
<211> LENGTH: 121
<212> TYPE: PRT
<213> ORGANISM: Homo sapience

<400> SEQUENCE: 117

Gln Val Gln Leu Val Gln Ser Gly Ala Asp Val Lys Lys Pro Gly Ser
1               5                   10                  15

Ser Val Arg Val Ser Cys Lys Ala Ser Gly Arg Thr Phe Gly Asn Tyr
            20                  25                  30

Ala Ile Ser Trp Val Arg Gln Ala Pro Gly Gln Gly Leu Glu Trp Met
        35                  40                  45

Gly Gly Ile Thr Pro Ile Phe Gly Ala Ala Asn Tyr Ala Gln Lys Phe
    50                  55                  60

Gln Gly Arg Val Thr Ile Ser Ala Asp Leu Ser Thr Thr Met Val Tyr
65                  70                  75                  80

Met Asp Leu Ser Ser Leu Arg Ser Asp Asp Thr Ala Phe Tyr Tyr Cys
                85                  90                  95

Ala Gly His Pro Thr Tyr Tyr Tyr Gly Ser Pro Met Asp Tyr Trp Gly
            100                 105                 110

Gln Gly Thr Leu Val Thr Val Ser Ser
        115                 120

<210> SEQ ID NO 118
<211> LENGTH: 121
<212> TYPE: PRT
<213> ORGANISM: Homo sapience

<400> SEQUENCE: 118

Gln Val Gln Leu Val Gln Ser Gly Ala Asp Val Lys Lys Ala Gly Ser
1               5                   10                  15

Ser Val Lys Val Ser Cys Lys Ala Ser Gly Arg Thr Phe Gly Asn Tyr
            20                  25                  30

Ala Ile Ser Trp Val Arg Gln Ala Pro Gly Gln Gly Leu Glu Trp Met
        35                  40                  45

Gly Gly Ile Thr Pro Ile Phe Gly Ala Ala Asn Tyr Ala Gln Lys Phe
    50                  55                  60

Gln Gly Arg Val Thr Ile Ser Ala Asp Leu Ser Thr Arg Met Val Tyr
65                  70                  75                  80

Met Asp Leu Ser Ser Leu Arg Ser Asp Asp Thr Ala Phe Tyr Tyr Cys
                85                  90                  95

Ala Gly His Pro Met Tyr His Tyr Gly Ser Ala Met Asp Tyr Trp Gly
            100                 105                 110

Gln Gly Thr Leu Val Thr Val Ser Ser
        115                 120

<210> SEQ ID NO 119
<211> LENGTH: 121
<212> TYPE: PRT
<213> ORGANISM: Homo sapience

<400> SEQUENCE: 119

Gln Val Gln Leu Val Gln Ser Gly Ala Glu Val Lys Lys Pro Gly Ser
1               5                   10                  15

Ser Val Lys Val Ser Cys Glu Ala Ser Gly Ala Thr Phe Ser Ser Asn
            20                  25                  30

Ala Phe Ser Trp Val Arg Gln Ala Pro Gly Gln Gly Pro Glu Trp Met
        35                  40                  45

Gly Gly Ile Ile Thr Met Phe Arg Lys Ala Glu Tyr Ala Gln Lys Phe
50                  55                  60

Gln Gly Arg Val Thr Ile Thr Ala Gly Glu Leu Gly Ser Thr Ala Tyr
65                  70                  75                  80

Met Glu Val Arg Ser Leu Thr Phe Glu Asp Thr Ala Val Tyr Tyr Cys
                85                  90                  95

Ala Arg His Ser Gly Tyr His Leu Ile Gly Tyr Phe Asp Ser Trp Gly
            100                 105                 110

Gln Gly Thr Leu Val Thr Val Ser Ser
        115                 120

<210> SEQ ID NO 120
<211> LENGTH: 122
<212> TYPE: PRT
<213> ORGANISM: Homo sapience

<400> SEQUENCE: 120

Gln Val Gln Leu Val Gln Ser Gly Ala Glu Val Arg Lys Pro Gly Ser
1               5                   10                  15

Ser Val Lys Val Ser Cys Lys Ala Ser Gly Val Ile Phe Ile Lys Phe
            20                  25                  30

Ala Ile Ser Trp Val Arg Gln Ala Pro Gly Gln Gly Leu Glu Trp Met
        35                  40                  45

Gly Gly Ile Ile Pro Met Phe Gly Thr Thr Asn Tyr Ala Gln Lys Phe
50                  55                  60

Gln Gly Arg Val Thr Ile Thr Ala Asp Gly Ser Thr Asn Thr Val Tyr
65                  70                  75                  80

Met Glu Leu Ser Ser Leu Thr Ser Glu Asp Thr Ala Val Tyr Tyr Cys
                85                  90                  95

Ala Lys Glu Glu Gly Tyr Tyr Tyr Gly Ser Gly Pro Leu Asp Ser Trp
            100                 105                 110

Gly Gln Gly Thr Leu Val Thr Val Ser Ser
        115                 120

<210> SEQ ID NO 121
<211> LENGTH: 122
<212> TYPE: PRT
<213> ORGANISM: Homo sapience

<400> SEQUENCE: 121

Gln Val Gln Leu Gln Gln Ser Gly Ala Glu Val Lys Gln Pro Gly Ser
1               5                   10                  15

Ser Val Lys Val Ser Cys Lys Ala Ser Gly Gly Ile Phe Arg Ser Asn
            20                  25                  30

Ala Ile Ser Trp Val Arg Gln Ala Pro Gly Gln Gly Leu Glu Trp Met
        35                  40                  45

Gly Gly Ile Val Ala Leu Phe Gly Thr Ala Asn Tyr Ala Gln Lys Phe
50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Arg Tyr Tyr Cys
                85                  90                  95

Ala Arg Asn Ser Gly Tyr His Ile Ser Gly Phe Tyr Leu Asp Tyr Trp
            100                 105                 110

Gly Gln Gly Thr Leu Val Thr Val Ser Ser
            115                 120

<210> SEQ ID NO 122
<211> LENGTH: 122
<212> TYPE: PRT
<213> ORGANISM: Homo sapience

<400> SEQUENCE: 122

Gln Val Gln Leu Gln Glu Ser Gly Ala Glu Val Lys Lys Pro Gly Ser
1               5                   10                  15

Ser Val Lys Val Ser Cys Lys Ala Ser Gly Gly Pro Phe Arg Ser His
            20                  25                  30

Ala Ile Ser Trp Val Arg Gln Ala Ala Gly Gln Gly Leu Glu Trp Met
        35                  40                  45

Gly Gly Ile Thr Ala Val Phe Gly Thr Ala Asn Tyr Ala Gln Lys Phe
    50                  55                  60

Gln Gly Arg Val Thr Ile Thr Ala Asp Glu Ser Thr Asn Ile Val Ser
65                  70                  75                  80

Met Glu Leu Ser Ser Leu Arg Ser Glu Asp Thr Ala Ile Tyr Tyr Cys
                85                  90                  95

Ala Arg Ser Leu Gly Tyr His Thr Gln Tyr Asn Gly Met Asp Val Trp
            100                 105                 110

Gly Gln Gly Thr Thr Val Thr Val Ser Ser
            115                 120

<210> SEQ ID NO 123
<211> LENGTH: 124
<212> TYPE: PRT
<213> ORGANISM: Homo sapience

<400> SEQUENCE: 123

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Ile Phe Arg Lys Asn
            20                  25                  30

Ala Ile Ser Trp Val Arg Gln Ala Pro Gly Gln Gly Leu Glu Trp Met
        35                  40                  45

Gly Gly Ile Ser Ala Ile Phe Gly Thr Ala Asn Tyr Ala Gln Lys Phe
    50                  55                  60

Gln Gly Arg Val Thr Ile Thr Ala Asp Glu Ser Ser Asn Thr Val Tyr
65                  70                  75                  80

Met Asp Leu Ser Arg Leu Arg Ser Glu Asp Thr Ala Ile Tyr Tyr Cys
                85                  90                  95

Ala Ser His Pro Thr Tyr His Phe Asp Lys Ser Gly Tyr Arg Phe Asp
            100                 105                 110

Ser Trp Gly Gln Gly Thr Leu Val Thr Val Ser Ser
            115                 120

<210> SEQ ID NO 124
<211> LENGTH: 124
<212> TYPE: PRT
<213> ORGANISM: Homo sapience

<400> SEQUENCE: 124

-continued

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ile Phe Asn Ser Asn
            20                  25                  30

Ala Ile Ser Trp Val Arg Gln Ala Pro Gly Gln Gly Leu Glu Trp Met
        35                  40                  45

Gly Gly Ile Gly Ile Phe Gly Thr Ala Asn Tyr Ala Gln Lys Phe
    50                  55                  60

Gln Gly Arg Val Thr Ile Ala Ala Asp Gln Ser Thr Asn Thr Val Phe
65                  70                  75                  80

Met Glu Leu Ser Ser Leu Thr Ser Glu Asp Thr Ala Val Tyr Phe Cys
            85                  90                  95

Ala Arg Ser Arg Gly Tyr Ser Phe Gly Tyr Gly Thr Asp Tyr Phe Asp
            100                 105                 110

Tyr Trp Gly Gln Gly Thr Leu Val Thr Val Ser Ser
            115                 120

<210> SEQ ID NO 125
<211> LENGTH: 124
<212> TYPE: PRT
<213> ORGANISM: Homo sapience

<400> SEQUENCE: 125

Gln Val Gln Leu Val Gln Ser Gly Ser Glu Val Lys Lys Pro Gly Ser
1               5                   10                  15

Ser Val Lys Val Ser Cys Lys Ala Ser Arg Gly Ile Phe Ser Ser Tyr
            20                  25                  30

Ala Ile Ser Trp Val Arg Gln Ala Pro Gly Gln Gly Leu Glu Trp Met
        35                  40                  45

Gly Ala Val Ile Pro Met Phe Gly Thr Leu Lys Tyr Ala Glu Asn Phe
    50                  55                  60

Gln Gly Arg Ile Thr Ile Ser Ala Asp Lys Ser Met Ser Ala Ala Tyr
65                  70                  75                  80

Met Glu Leu Ser Ser Leu Arg Ser Glu Asp Thr Ala Val Tyr Tyr Cys
            85                  90                  95

Ala Arg Asn Tyr Tyr Gly Ser Gly Thr Tyr Phe Asn Asp Ala Phe Asp
            100                 105                 110

Ile Trp Gly Gln Gly Thr Met Val Thr Val Ser Ser
            115                 120

<210> SEQ ID NO 126
<211> LENGTH: 126
<212> TYPE: PRT
<213> ORGANISM: Homo sapience

<400> SEQUENCE: 126

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Phe
            20                  25                  30

Ser Thr Tyr Thr Ile Ser Trp Val Arg Gln Ala Pro Gly Gln Gly Leu
        35                  40                  45

Glu Trp Met Gly Arg Ser Ile Pro Leu Leu Gly Ile Thr Asn Tyr Ala
    50                  55                  60

Gln Lys Phe Gln Gly Arg Val Thr Ile Thr Ala Asp Ile Ser Thr Ser
65                  70                  75                  80

-continued

```
Thr Ala Tyr Met Glu Leu Ser Ser Leu Arg Ser Glu Asp Thr Ala Val
                85                  90                  95
Tyr Tyr Cys Ala Arg Tyr Gln Ser Asp Tyr Asn Ser Glu Tyr
            100                 105                 110
Phe Gln His Trp Gly Gln Gly Thr Leu Val Thr Val Ser Ser
        115                 120                 125

<210> SEQ ID NO 127
<211> LENGTH: 296
<212> TYPE: DNA
<213> ORGANISM: Homo sapience

<400> SEQUENCE: 127
caggtgcagc tggtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaggg atcatcccta tctttggtac agcaaactac     180
gcacagaagt tccagggcag agtcacgatt accgcggacg aatccacgag cacagcctac     240
atggagctga gcagcctgag atctgaggac acggccgtgt attactgtgc gagaga         296

<210> SEQ ID NO 128
<211> LENGTH: 98
<212> TYPE: PRT
<213> ORGANISM: Homo sapience

<400> SEQUENCE: 128

Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
            35                  40                  45
Gly Gly Ile Ile Pro Ile Phe Gly Thr Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg

<210> SEQ ID NO 129
<211> LENGTH: 20
<212> TYPE: DNA
<213> ORGANISM: Artificial Sequence
<220> FEATURE:
<223> OTHER INFORMATION: primer T7ETZ

<400> SEQUENCE: 129
taatacgact cactataggg                                                   20
```